US012788639B2

(12) United States Patent
Öberg et al.

(10) Patent No.: US 12,788,639 B2
(45) Date of Patent: Nov. 10, 2026

(54) HYGIENE MONITORING DEVICE WITH A SENSING PANEL

(71) Applicant: Essity Hygiene and Health Aktiebolag, Gothenburg (SE)

(72) Inventors: Michael Öberg, Gothenburg (SE); Joshua Carney, Floda (SE); Henrik Pettersson-Falk, Harryda (SE); Anders Olsson, Gothenburg (SE)

(73) Assignee: ESSITY HYGIENE AND HEALTH AKTIEBOLAG, Gothenburg (SE)

(*) Notice: Subject to any disclaimer, the term of this patent is extended or adjusted under 35 U.S.C. 154(b) by 725 days.

(21) Appl. No.: 17/413,669

(22) PCT Filed: Dec. 20, 2018

(86) PCT No.: PCT/EP2018/086218
§ 371 (c)(1),
(2) Date: Jun. 14, 2021

(87) PCT Pub. No.: WO2020/126000
PCT Pub. Date: Jun. 25, 2020

(65) Prior Publication Data

US 2022/0054326 A1 Feb. 24, 2022

(51) Int. Cl.
*A61F 13/42* (2006.01)
*G01N 27/02* (2006.01)

(52) U.S. Cl.
CPC ............ *A61F 13/42* (2013.01); *G01N 27/02* (2013.01); *A61F 2013/424* (2013.01)

(58) Field of Classification Search
CPC ... A61F 13/42; A61F 2013/424; G01N 27/02; G01N 27/048; A61B 5/053; A61B 5/207;
(Continued)

(56) References Cited

U.S. PATENT DOCUMENTS 5,845,644 A 12/1998 Hughes et al.
7,667,608 B2 2/2010 Ales et al.
(Continued)

FOREIGN PATENT DOCUMENTS

CN 1402768 A 3/2003
CN 102481112 A 5/2012
(Continued)

OTHER PUBLICATIONS

Brazilian Application No. BR112021008140-2; Brazilian Search Report dated Sep. 7, 2022; 4 pages.
(Continued)

*Primary Examiner* — Rebecca E Eisenberg
*Assistant Examiner* — Kate Elizabeth Strachan
(74) *Attorney, Agent, or Firm* — CANTOR COLBURN LLP

(57) ABSTRACT

There is provided a hygiene monitoring device including a sensing panel. The sensing panel has an elongate flexible panel defining a longitudinal axis. The elongate flexible panel includes a first pair of plates spaced apart from each other in a direction crossing the longitudinal axis. The elongate flexible panel also includes a second pair of plates spaced apart from each other in a direction crossing the longitudinal axis. The first pair of plates and the second pair of plates are disposed on a flexible substrate of the elongate flexible panel. Each plate of the first pair of plates and each plate of the second pair of plates is elongate along the longitudinal axis of the elongate flexible panel. The hygiene monitoring device is configured to measure the impedance between two of the plates.

19 Claims, 13 Drawing Sheets

(58) Field of Classification Search
CPC .............. A61B 5/4255; A61B 2505/09; A61B 2562/0209; A61B 2562/029; A61B 2562/164; A61B 5/6808
See application file for complete search history.

(56) References Cited

U.S. PATENT DOCUMENTS

| | | | |
|---|---|---|---|
| 8,663,106 B2 | 3/2014 | Stivoric et al. | |
| 8,816,149 B2 | 8/2014 | Richardson et al. | |
| 9,904,562 B2 | 2/2018 | Bergström et al. | |
| 11,173,073 B2 | 11/2021 | Macnaughton et al. | |
| 2004/0078219 A1* | 4/2004 | Kaylor | G16H 40/67 600/300 |
| 2005/0156744 A1 | 7/2005 | Pires | |
| 2005/0245839 A1 | 11/2005 | Stivoric et al. | |
| 2007/0083174 A1 | 4/2007 | Ales et al. | |
| 2007/0252713 A1 | 11/2007 | Rondoni et al. | |
| 2008/0132859 A1 | 6/2008 | Pires | |
| 2008/0171920 A1 | 7/2008 | Teller et al. | |
| 2008/0269702 A1 | 10/2008 | Ales et al. | |
| 2010/0245114 A1* | 9/2010 | Celik-Butler | G01D 11/245 340/8.1 |
| 2012/0149996 A1 | 6/2012 | Stivoric et al. | |
| 2012/0268278 A1 | 10/2012 | Lewis et al. | |
| 2013/0018340 A1* | 1/2013 | Abraham | A61F 13/42 604/361 |
| 2013/0268231 A1 | 10/2013 | Sato | |
| 2013/0303867 A1 | 11/2013 | Elfstrom et al. | |
| 2013/0307570 A1 | 11/2013 | Bosaeus et al. | |
| 2014/0218057 A1* | 8/2014 | White | G01R 27/2605 29/25.42 |
| 2014/0350503 A1 | 11/2014 | Bosaeus et al. | |
| 2014/0371702 A1 | 12/2014 | Bosaeus et al. | |
| 2016/0080841 A1 | 3/2016 | Bergström et al. | |
| 2016/0361209 A1 | 12/2016 | Mashin-Chi et al. | |
| 2017/0307458 A1 | 10/2017 | Landmann | |
| 2018/0333306 A1 | 11/2018 | Ahong et al. | |
| 2019/0247650 A1 | 8/2019 | Tran | |
| 2020/0060899 A1 | 2/2020 | Neeley et al. | |
| 2020/0323285 A1 | 10/2020 | Longinotti-Buitoni et al. | |
| 2020/0352794 A1 | 11/2020 | Curran et al. | |
| 2021/0113130 A1 | 4/2021 | Tran | |
| 2022/0015956 A1 | 1/2022 | Öberg et al. | |
| 2026/0079033 A1 | 3/2026 | Pettersson-Falk | |

FOREIGN PATENT DOCUMENTS

| | | | | |
|---|---|---|---|---|
| CN | 102573713 A | 7/2012 | | |
| CN | 103269667 A | 8/2013 | | |
| CN | 103269668 A | 8/2013 | | |
| CN | 103327944 A | 9/2013 | | |
| CN | 103561705 A | 2/2014 | | |
| CN | 104066409 A | 9/2014 | | |
| CN | 107530214 A | 1/2018 | | |
| CO | 08070222 | 11/2008 | | |
| EP | 1995579 A2 | 11/2008 | | |
| EP | 3415130 A1 | 12/2018 | | |
| GB | 2540986 A | * | 2/2017 | A61B 5/0531 |
| JP | S48123527 | 10/1973 | | |
| JP | S50069190 U | 6/1975 | | |
| JP | 2000093448 A | 4/2000 | | |
| JP | 2002082080 A | 3/2002 | | |
| JP | 2006296566 A | 11/2006 | | |
| JP | 2009006180 A | 1/2009 | | |
| JP | 2009031264 A | 2/2009 | | |
| JP | 2013039158 A | 2/2013 | | |
| JP | 2013218454 A | 10/2013 | | |
| JP | 2016119922 A | 7/2016 | | |
| JP | 2016195792 A | 11/2016 | | |
| JP | 2018501864 A | 1/2018 | | |
| KR | 101667120 B1 | 10/2016 | | |
| WO | 2006047815 A1 | 5/2006 | | |
| WO | 2007128038 A1 | 11/2007 | | |
| WO | 2010049827 A2 | 5/2010 | | |
| WO | 2010123425 A1 | 10/2010 | | |
| WO | 2011004165 A1 | 1/2011 | | |
| WO | 2011054045 A1 | 5/2011 | | |
| WO | 2012084924 A1 | 6/2012 | | |
| WO | 2012084987 A2 | 6/2012 | | |
| WO | 2012114208 A1 | 8/2012 | | |
| WO | WO-2012166765 A1 | * | 12/2012 | A61F 13/42 |
| WO | 2015102084 A1 | 7/2015 | | |
| WO | 2016090492 A1 | 6/2016 | | |
| WO | 2017152687 A1 | 9/2017 | | |
| WO | 2019096413 A1 | 5/2019 | | |
| WO | 2020125999 A1 | 6/2020 | | |
| WO | 2020126000 A1 | 6/2020 | | |
| WO | 2021004598 A1 | 1/2021 | | |
| WO | 2024061465 A1 | 3/2024 | | |

OTHER PUBLICATIONS

Brazilian Application No. BR112021011142-5; Brazilian Search Report dated Sep. 7, 2022; 4 pages.

Canadian Application No. 3,119,685; Canadian Office Action dated Oct. 13, 2022; 6 pages.

Canadian Application No. 3, 123,929; Canadian Office Action dated Oct. 6, 2022; 4 pages.

Canadian Application No. 3, 134, 131; Canadian Office Action dated Nov. 24, 2022; 4 pages.

Chinese Application No. 201880100107.X; Chinese Office Action dated Oct. 26, 2022; 11 pages.

European Application No. 18826035.0; Communication pursuant to Article 94(3) EPC dated Jan. 3, 2023; 3 pages.

European Patent Office, International Search Report and Written Opinion of the International Searching Authority, International Application No. PCT/EP2018/086217, mailed Mar. 20, 2019 (13 pages).

European Patent Office, International Search Report and Written Opinion of the International Searching Authority, International Application No. PCT/EP2018/086218, mailed Jun. 25, 2019 (13 pages).

International Searching Authority, Search Report and Written Opinion issued in PCT/EP2018/086217, mailed Mar. 20, 2019 (13 pages).

International Searching Authority, Search Report and Written Opinion issued in PCT/EP2018/086218, mailed Jun. 25, 2019 (13 pages).

Japanese Application No. 2021-535834; Japanese Office Action with English translation mailed Sep. 12, 2022; 12 pages.

Japanese Application No. 2021-560984; Japanese Office Action with English Translation dated Oct. 31, 2022; 14 pages.

Korean Application No. 10-2021-7019765; Korean Office Action with English Translation dated Dec. 13, 2022; 22 bages.

Australian Government, IP Australia, Examination report No. 1 for standard patent application, Application No. 2018454396, mailed Oct. 29, 2021 (4 pages).

European Patent Office, International Search Report and Written Opinion of the International Searching Authority, PCT/EP2019/059672, mailed Jan. 27, 2020 (14 pages).

Australian Government, IP Australia, Examination report No. 1 for standard patent application, Application No. 2018454245, mailed Mar. 31, 2022 (5 pages).

National Intellectual Property Administration (CNIPA) of the People's Republic of China, Office Action, Application No. 201880100095.0, dated Aug. 10, 2022 (26 pages).

National Intellectual Property Administration (CNIPA) of the People's Republic of China, Notification of the First Office Action, Application No. 201880100107.X, dated Dec. 2, 2021 (15 pages).

Australian Government, IP Australia, Examination report No. 1 for standard patent application, Application No. 2018454245, mailed Oct. 22, 2021 (5 pages).

National Intellectual Property Administration (CNIPA) of the People's Republic of China, Notification of the First Office Action, Application No. 201880100095.0, dated Dec. 2, 2021 (26 pages).

European Application No. 18826354.5-1102; Communication pursuant to Article 94(3) EPC dated Oct. 20, 2023; 3 pages.

(56) References Cited

OTHER PUBLICATIONS

Japanese Application No. 2021-535834; Decision of Rejection dated Aug. 21, 2023; 4 pages.
Japanese Application No. 2021-535834; Decision to Reject the Amendments dated Aug. 21, 2023; 9 pages.
Japanese Application No. 2021-560984; Decision of Rejection dated May 29, 2023; 8 pages.
Australian Application No. 2018454396; Office Action dated Mar. 15, 2022; 4 pages.
Chinese Application No. 201880100107.X; Office Action dated Jun. 28, 2022; 12 pages.
Japanese Application No. 2021-531773; Office Action with English Translation dated May 9, 2022; 11 pages.
Japanese Application No. 2021-531773; Office Action with English Translation dated Nov. 14, 2022; 9 pages.
Korean Application No. 10-2021-7018888; Korean Office Action with English Translation dated Dec. 12, 2022; 18 pages.
Canadian Application No. 3,119,685; Canadian Office Action dated May 5, 2023; 4 pages.
Chinese Application No. 201880100107.X; Office Action with English Translation dated Mar. 25, 2023; 19 pages.
Colombian Application No. NC2021/0006510; Colombian Office Action with English translation dated Mar. 15, 2023; 28 pages.
Colombian Application No. NC2021/0006510; Colombian Office Action with English translation dated Nov. 25, 2022; 18 pages.
European Application No. 18826035.0; Third Party Observation filed Apr. 27, 2023; 22 pages.
European Application No. 18826035.0; Third Party Observation filed Apr. 28, 2023; 6 pages.
European Application No. 18826035.0; Third Party Observation filed Apr. 28, 2023; 9 pages.
Japanese Application No. 2021-531773; Decision to Grant with English Translation dated Feb. 14, 2023; 6 pages.
Japanese Application No. 2021-535834; Japanese Office Action with English translation mailed Mar. 27, 2023; 11 pages.
Korean Application No. 10-2021-7018888; Korean Office Action with English Translation dated Jun. 20, 2023; 3 pages.
Korean Application No. 10-2021-7019765; Korean Office Action with English Translation dated May 19, 2023; 23 pages.
Third Party Observation for European Application No. EP20180826035 dated Apr. 28, 2023 15:01; 9 pages.
Third Party Observation for European Application No. EP20180826035 dated Apr. 28, 2023 15:05; 6 pages.
Third Party Observation for European Application No. EP20180826035 dated Mar. 19, 2024 11:42; 9 pages.
Third Party Observation for European Application No. EP20180826035 dated Mar. 19, 2024 14:42; 2 pages.
Third Party Submission on European Application No. 3897496A1 filed on Apr. 28, 2023; 16 pages.
Third Party Submission on European Application No. EP3897496A1 dated Apr. 27, 2023; 22 pages.
Chinese Office Action issued in Chinese Application No. 201980095471.6 dated Dec. 13, 2023; 31 pages.
Non-Final Office Action issued in U.S. Appl. No. 17/413,670 dated Feb. 16, 2024, 63 pages.
Brazilian Search Report issued in Brazilian Application No. BR112021018767-7 dated Mar. 20, 2024.
Colombia Office Action issued in Application No. NC2021/0013791 dated Mar. 1, 2024 with English translation.
Notification of Grounds for Refusal issued in Korean Application No. 10-2021-7036456 forwarding date Mar. 22, 2024 with English translation.
Second Office Action issued in Chinese Application No. 201980095471.6 dated May 15, 2024 with English translation.
Final Office Action issued in United State U.S. Appl. No. 17/413,670 dated Jun. 27, 2024.
Colombian Office Action issued in Colombian Application No. NC/2021/0008642; dated Nov. 30, 2023; 14 pages.
Australian Application No. 2019440869; Examination Report 1 dated Dec. 18, 2024; 3 pages.
International Search Report & Written Opinion for International Application No. PCT/EP2022/076369; International Filing Date: Sep. 22, 2022; Date of Mailing: May 19, 2023; 15 pages.
Japanese Application No. 2023-138032; Office Action with English translation dated Dec. 2, 2024; 14 pages.
Non-Final Office Action issued in U.S. Appl. No. 17/439,993 dated Jan. 16, 2025 , 75 pages.
Colombian Application No. NC2021/0013791; Office Action with English translation dated Sep. 2, 2024; 38 pages.
U.S. Appl. No. 17/413,670; Non-Final Office Action dated Nov. 8, 2024; 22 pages.
Brazilian Application No. BR112021011142-5; Office Action dated Jan. 29, 2024; 8 pages.
Japanese Office Action, Application No. 2025-517439, mailed Mar. 24, 2026, 7 pages, with English Translation.

* cited by examiner

HYGIENE MONITORING DEVICE WITH A SENSING PANEL

CROSS-REFERENCE TO RELATED APPLICATION

This application is a national phase entry of, and claims priority to, International Application No. PCT/EP2018/086218, filed Dec. 20, 2018, which is incorporated herein by reference in its entirety.

TECHNICAL FIELD

This application relates to a hygiene monitoring device including a sensing panel, such as one having an elongate flexible panel.

BACKGROUND

A hygiene monitoring device may be used to monitor a hygienic state of a user. For example, a hygiene monitoring device may monitor a wetness level, a temperature and/or a concentration of a particular substance associated with the user. In certain known devices, the hygiene monitoring device is attached to an article which is worn by the user such that the hygiene monitoring device may monitor a hygienic state of the article. In some devices, the hygiene monitoring device transmits information relating to the monitored hygienic state of the user, such as a soiling event. Additionally or alternatively, in some devices, the hygiene monitoring device produces an alert, such as a sound, to notify a detection of soiling event.

Certain hygiene monitoring devices comprise a sensing panel with one or more sensing plates, which is configured to be attached to the surface of the article or within the article. As such sensing panels may need to conform to the shape of the article, which may change depending on the movements of the user, the sensing panel may be flexible.

Typical sensing plates are square or circular and are disposed such that they are offset along the length of the sensing panel. Such a configuration is disclosed in Applicant's co-pending application PCT/EP2017/079675.

However, due to the typical curved shapes taken by the sensing panel when the article is worn by a user, unwanted coupling between the sensing plates of the sensing panel may occur in these typical arrangements. Especially when the sensing plates are adapted to measure an impedance between adjacent plates, it is possible for unintended coupling to occur with additional plates which are remote from the adjacent plates. In particular, typical arrangements of the plates tend to be sensitive to unwanted factors, such as the user themselves and/or the clothing worn by the user, rather than being sensitive to the state of the article, which is used to determine the hygienic state of the article.

Accordingly, it would be desirable to provide a hygiene monitoring device which allows for more accurate detection of a hygienic state.

SUMMARY

The technical objects identified above are achieved by providing a hygiene monitoring device according to a first embodiment. The hygiene monitoring device comprises a sensing panel. The sensing panel comprises an elongate flexible panel defining a longitudinal axis. The elongate flexible panel comprises a first pair of plates spaced apart from each other in a direction crossing the longitudinal axis. The elongate flexible panel comprises a second pair of plates spaced apart from each other in a direction crossing the longitudinal axis. The first pair of plates and the second pair of plates are disposed on a flexible substrate of the elongate flexible panel. Each plate of the first pair of plates and each plate of the second pair of plates is elongate along the longitudinal axis of the elongate flexible panel. The first pair of plates is offset along the longitudinal axis with respect to the second pair of plates. The hygiene monitoring device is configured to measure the impedance between two of the plates.

It has been found that by using elongate plates which are configured to measure an impedance therebetween allows for the electric field lines between the plates to be more localized to regions in the immediate vicinity of the hygiene monitoring device (i.e., the article), regardless of the curved shaped taken by the sensing panel. Accordingly, variations in the dielectric constant and resistance (e.g., caused by the user or their clothing) in areas other than the immediate vicinity of the hygiene monitoring device do not have a great impact on the impedance between the plates.

Hence, with such a configuration, a hygiene monitoring device is provided which allows for more accurate detection of a hygienic state.

In certain embodiments, the plates of the first pair of plates partially or fully overlap along the longitudinal axis of the elongate flexible panel. In certain embodiments, the plates of the second pair of plates partially or fully overlap along the longitudinal axis of the elongate flexible panel. In other words, the plates of the first pair of plates and/or the plates of the second pair of plates have partially of fully overlapping longitudinal extents along the longitudinal axis of the elongate flexible panel.

As used herein 'spaced apart' means that the plates do not contact each other. Throughout this disclosure, none of the plates contact one another.

In certain embodiments, the plates of the first pair of plates lie in the same plane. In certain embodiments, the plates of the second pair of plates lie in the same plane. In other words, the plates of the first pair of plates and/or the plates of the second pair of plates are coplanar.

In certain embodiments, the plates of the first pair of plates lie in the same plane as the flexible substrate. In certain embodiments, the plates of the second pair of plates lie in the same plane as the flexible substrate.

In certain embodiments, the plates of the pair of spaced apart plates are spaced apart along a transverse axis of the elongate flexible panel which is perpendicular to the longitudinal axis.

The longitudinal axes of the plates are parallel to the longitudinal axis of the elongate flexible panel.

Throughout this disclosure the measurement of impedance may optionally be a measurement and/or a calculation of the magnitude of the impedance.

In certain embodiments, the plates are disposed on one side of the flexible substrate, and wherein the elongate flexible panel further comprises a grounding plate disposed on the other side of the flexible substrate.

Using a grounding plate disposed on the opposite side of the plates results in the electric fields between the plates being largely localized to only one side of the hygiene monitoring device.

Accordingly, the measurements carried out by the hygiene monitoring device are primarily sensitive to only one side of the device, which means that the dielectric constant and resistance on the other side of the device does not significantly impact the measured impedance.

The dielectric constant and resistance on the other side of the plates may tend to change frequently (for example, due to a change in clothing worn by the user). However, with the above configuration, the measured impedance is not significantly affected by these changes, which results in improved accuracy of detection.

In certain embodiments, the grounding plate partially or fully overlaps the plates in the plane of the flexible substrate.

With this configuration, the grounding plate may more optimally localize the electric fields to only one side of the hygiene monitoring device.

In certain embodiments, the longitudinal axis of each of the plates of the first pair of plates are parallel. Additionally or alternatively, the longitudinal axis of each of the plates of the second pair of plates are parallel. The plates of the first pair of plates may be parallel with the plates of the second pair of plates.

With such a configuration, it is possible to further constrain the electric fields between the plates, which further improves the accuracy of the detection of the hygienic state.

In certain embodiments, the longitudinal axis of each of the plates of the first pair of plates converge. Additionally or alternatively, the longitudinal axis of each of the plates of the second pair of plates converge.

With such a configuration, the electric fields are more localized towards the end of the plates which are closer to each other, which results in a more localized sensitivity region towards this end of the plates. Accordingly, the plates may be arranged to be sensitive to two different types of exudate on opposite sides of the plates.

In certain embodiments, at least one of the plates has a generally rectangular, tapered or curved shape.

In certain embodiments, at least one of the plates has a generally rectangular shape with rounded corners.

In certain embodiments, the impedance between the plates of the first pair of plates in free space has a first value. The impedance between the plates of the second pair of plates in free space has a second value. The first value and the second value are different.

Throughout this disclosure, a comparison between the impedance between any two pairs of plates is a reference to a comparison between the impendences measured at the same frequency between the two pairs of plates. For example, the impedance of each pair of plates may be measured at one and the same frequency, such as 10 kHz, 20 kHz, 30 kHz, 40 kHz, 50 kHz, 60 kHz or 70 kHz.

As the properties of the two pairs of plates are different such that their impedance in free space is different, it is possible to tailor each pair of plates so as to be more sensitive to a particular type of soiling. For example, the first pair of plates may be configured such that they are more sensitive to the measurements of urine, whereas the second pair of plates may be configured such that they are more sensitive to the measurement of fecal matter.

In certain embodiments, at least one or both of the plates of the first pair of plates has a different shape from at least one or both of the plates of the second pair of plates. At least one or both of the plates of the first pair of plates may have a different width and/or length from at least one or both of the plates of the second pair of plates.

In certain embodiments, the plates of the first pair of plates are spaced apart a first distance. The plates of the second pair of plates are spaced apart a second distance. The first distance and the second distance are different.

In certain embodiments, the hygiene monitoring device comprises a monitoring unit electrically connected to each of the plates. The monitoring unit is configured to measure the impedance between the two plates.

In certain embodiments, the two plates are plates in the same pair of plates.

With such a configuration, the coupling between the two plates is mainly reactive which enables improved resolution when measuring low degrees of saturation in a wearable absorbent hygiene article.

In certain embodiments, the two plates are plates in different pairs of plates.

With such a configuration, the coupling between the two plates is mainly resistive which enables improved resolution when measuring high degrees of saturation in a wearable absorbent hygiene article.

Specifically, as the two plates are in different pairs of plates, the two plates have a greater spacing along the longitudinal axis of the elongate flexible panel as opposed to the situation where the two plates are in the same pair. With larger degrees of saturation in the wearable hygiene article, a large volume of exudate forms in the wearable hygiene article to form an absorbent material (i.e., super absorbent material)/exudate gel and tends to extend in size along the length of the article, with the two plates exciting opposing sides of the volume of exudate. With the above configuration, the coupling between the two plates is mainly resistive, and, therefore, as the size of the volume of exudate grows, the resistance between the two plates systematically drops, which allows for measurement with a higher resolution.

In certain embodiments, the first plate of the two plates is on a first side of the elongate flexible panel along a direction perpendicular to the longitudinal axis. The second plate of the two plates is on a second, opposite side of the elongate flexible panel along the direction perpendicular to the longitudinal axis.

In certain embodiments, the two plates are offset from each other in a direction crossing the longitudinal axis. In one embodiment, the two plates are opposite to each other along a direction perpendicular to the longitudinal axis.

With such configurations, as the two plates are disposed diagonally across the elongate flexible panel, the sensitivity of the hygiene monitoring device may be arranged to extend across a larger portion of a wearable absorbent hygiene article.

In certain embodiments, the elongate flexible panel further comprises a third pair of plates spaced apart from each other in a direction crossing the longitudinal axis, the third pair of plates being disposed on the flexible substrate. At least one of the two plates is a plate in the third pair of plates.

With such a configuration, the accuracy of the measurements may be improved.

In certain embodiments, the third pair of plates is offset along the longitudinal axis with respect to each of the first and second pair of plates.

The second pair of plates is disposed along the longitudinal axis between the first pair of plates and the second pair of plates.

In certain embodiments, one of the two plates is a plate in the first pair of plates and the other of the two plates is a plate in the third pair of plates.

With such a configuration, the coupling between the two plates is mainly resistive which enables improved resolution when measuring high degrees of saturation in a wearable absorbent hygiene article.

Specifically, in a similar manner as described above, as the two plates are in opposite pairs of plates, the two plates have a greater spacing along the longitudinal axis of the elongate flexible panel as opposed to the situation where the two plates are in the same pair/neighboring pairs. With larger degrees of saturation in the wearable hygiene article, a large volume of exudate forms in the wearable hygiene article to form an absorbent material (i.e., super absorbent material)/exudate gel and tends to extend in size along the length of the article, with the two plates exciting opposing sides of the volume of exudate. With the above configuration, the coupling between the two plates is mainly resistive, and, therefore, as the size of the volume of exudate grows, the resistance between the two plates systematically drops, which allows for measurement with a higher resolution.

In certain embodiments, the two plates are plates in the same pair of plates. The hygiene monitoring device is further configured to measure a second impedance between a second two of the plates. The second two plates may be plates in different pairs of plates.

In certain embodiments, the hygiene monitoring device is configured to individually measure the impedance between each and every possible combination of two plates.

In certain embodiments, the hygiene monitoring device is configured to individually measure the impedance between two, three, four, five or six combinations of two plates.

With such configurations, as different pairings of the two measured plates are particularly suited for measuring certain hygienic events and/or levels of saturation in the wearable absorbent hygiene article, the hygiene monitoring device may base the determination of the hygienic state on the pairing of plates (or combination of pairings) which provides an accurate assessment of the hygienic state.

In certain embodiments, the elongate flexible panel further comprises an insulating layer which entirely covers the plates.

With such a configuration, a purely resistive coupling between the two plates may be avoided, which improves the value of the impedance measurements.

In certain embodiments, the hygiene monitoring device is configured to be attachable to a wearable absorbent hygiene article.

In certain embodiments, the hygiene monitoring device is configured to be removably attachable to a wearable absorbent hygiene article.

In certain embodiments, the hygiene monitoring device comprises a hook and/or loop type fastener configured to be removably attachable to the wearable absorbent hygiene article.

In certain embodiments, the hook and/or loop type fastener is disposed on the elongate flexible panel. The hook and/or loop type fastener may be disposed on the plates.

In certain embodiments, the hygiene monitoring device is configured to be attachable to a wearable absorbent hygiene article. The hygiene monitoring device comprises a pressure sensitive adhesive configured to allow the hygiene monitoring device to be attached to the wearable absorbent hygiene article. The pressure sensitive adhesive may be disposed on the elongate flexible panel. The pressure sensitive adhesive may be disposed on the plates.

In certain embodiments, at least one plate or all plates have a width $W_P$ in the transverse direction T of the elongate flexible panel. The width $W_P$ may be between 4 mm and 7 mm, and preferably 6 mm.

In certain embodiments, at least one plate or all plates have a length $L_P$ in the longitudinal direction L of the elongate flexible panel. The length $L_P$ may be between 45 mm to 1000 mm, preferably between 180 mm and 220 mm, and more preferably 200 mm.

The plates in at least one pair or all pairs of plates are spaced apart along the transverse direction T of the elongate flexible panel by a distance $W_{SA}$.

The distance $W_{SA}$ may be between 4 mm and 7 mm, and preferably 6 mm.

The plates in at least one pair or all pairs of plates are spaced apart along the longitudinal axis with respect to the plates of the second pair of plates 15*a*, 15*b* by a distance $L_{SA}$. The distance $L_{SA}$ may be between 4 mm and 7 mm, and preferably 6 mm.

Preferably, the distance $W_{SA}$ and the distance $L_{SA}$ are the same.

The elongate flexible panel has a length $L_{SP}$ in the longitudinal direction L. In certain embodiments, the length $L_P$ may be between 20% to 40%, preferably 30% of the length $L_{SP}$.

In a second embodiment of the present invention, there is provided a system comprising a wearable absorbent hygiene article defining a front waist region, a back waist region, a crotch region and a longitudinal axis. The wearable absorbent hygiene article comprises a liquid permeable top layer adapted to face the wearer during use. The wearable absorbent hygiene article comprises a back layer opposite to the top layer. The wearable absorbent hygiene article comprises an absorbent core in at least the crotch region and located between the top layer and the back layer. The system further comprises the hygiene monitoring device of any embodiment described herein.

The longitudinal axis of the wearable absorbent hygiene article extends from the front waist region to the back waist region.

The back layer is liquid impermeable, and, optionally, the back layer is breathable or vapor permeable.

With such a configuration, the hygienic state of the article may more accurately be detected.

In certain embodiments, the hygiene monitoring device is configured to be attachable to the back layer of the wearable absorbent hygiene article.

The hygiene monitoring device is configured to be attachable to the outside surface of the back layer. Specifically, the hygiene monitoring device is configured to be attachable to the surface of the back layer which is opposite to the surface of the back layer facing the absorbent core.

In certain embodiments, the hygiene monitoring device is configured to be removably attachable to the back layer of the wearable absorbent hygiene article.

In certain embodiments, the hygiene monitoring device and the back layer each comprise corresponding hook and loop type fasteners.

In certain embodiments, the elongate flexible panel is adapted such that the longitudinal axis of the elongate flexible panel may be parallel with the longitudinal axis of the wearable absorbent hygiene article.

In certain embodiments, the hygiene monitoring device is attached to the wearable absorbent hygiene article such that the longitudinal axis of the elongate flexible panel is parallel with the longitudinal axis of the wearable absorbent hygiene article.

With such configurations, as the wearable absorbent hygiene article tends to be curved during normal use along the longitudinal axis of the article, these arrangements allow more accurate detection of the hygienic state when the article is curved during typical use of the article.

In certain embodiments, the plates are configured to be disposed entirely within the area defined by the absorbent core.

In certain embodiments, the absorbent core has a core length along the longitudinal axis. The extent of the plates along the longitudinal axis of the elongate flexible panel defines a sensing length. In certain embodiments, the sensing length is 50% to 100% of the core length.

It has been found that with typical sensing plates (square or circular), as the sensing area is less localized to the absorbent article, longer sensing strips result in greater errors due to unwanted factors, such as the user themselves and/or the clothing worn by the user, rather than being sensitive to the state of the article itself.

It has been found that by using elongate plates and a sensing length that is 50% to 100% of the core length allows for a more complete detection of the state of the absorbent article, whilst improving accuracy of the measurements whilst the article is curved. In particular, the use of elongate plates allows for the electric field lines between the plates to be more localized to regions in the immediate vicinity of the hygiene monitoring device (i.e., the article), regardless of the curved shaped taken by the sensing panel, which in turn allows for a longer sensing length without compromising the accuracy.

Hence, with such a configuration, a hygiene monitoring device is provided which allows for more accurate and complete detection of a hygienic state when the hygiene monitoring device is curved.

In certain embodiments, the sensing length is 15 cm to 40 cm, or wherein the sensing length is 40 cm to 80 cm.

In certain embodiments, the sensing length is 60% to 95% of the core length.

With such a configuration, the hygiene monitoring device is further optimized to allow for more accurate and complete detection of a hygienic state when the hygiene monitoring device is curved.

In certain embodiments, the sensing length is 18 cm to 38 cm, or wherein the sensing length is 38 cm to 76 cm.

In certain embodiments, the sensing length is 70% to 80% of the core length.

With such a configuration, the hygiene monitoring device is further optimized to allow for more accurate and complete detection of a hygienic state when the hygiene monitoring device is curved.

In certain embodiments, the sensing length is 21 cm to 32 cm, or wherein the sensing length is 32 cm to 64 cm.

In a third embodiment of the present invention, there is provided a kit comprising a wearable absorbent hygiene article defining a front waist region, a back waist region, a crotch region and a longitudinal axis. The wearable absorbent hygiene article comprises a liquid permeable top layer adapted to face the wearer during use. The wearable absorbent hygiene article comprises a back layer opposite to the top layer. The wearable absorbent hygiene article comprises an absorbent core in the crotch region and located between the top layer and the back layer. The kit further comprises the hygiene monitoring device of any embodiment described herein.

With such a configuration, the hygienic state of the article may more accurately be detected.

In a fourth embodiment of the present invention, there is provided a hygiene monitoring device adapted to be removably attached to a back layer of a wearable absorbent hygiene article. The hygiene monitoring device has a sensing panel. The sensing panel comprises an elongate flexible panel defining a longitudinal axis and comprising plates. The plates comprise a pair of plates spaced apart from each other. The plates are disposed on a flexible substrate of the elongate flexible panel. Each of the plates is elongate along the longitudinal axis of the elongate flexible panel. The hygiene monitoring device is configured to measure the impedance between two of the plates. The extent of the plates along the longitudinal axis of the elongate flexible panel defines a sensing length. The sensing length is 15 cm to 40 cm or 40 cm to 80 cm.

With such a configuration, a hygiene monitoring device is provided which allows for more accurate and complete detection of a hygienic state when the hygiene monitoring device is curved.

In a fifth embodiment of the present invention, there is provided a method carried out by the hygiene monitoring device of any of the embodiments described herein. The method comprises measuring the impedance between the two plates.

With such a method, it is possible to more accurately detect a hygienic state of the hygiene monitoring device.

In one implementation, the method further comprises measuring a second impedance between a second two of the plates.

With such a method, it is possible to discriminate between events localized to different positions in the device and and/or more accurately determine the hygienic event as different pairings of the two measured plates are particularly suited for measuring certain hygienic events and/or levels of saturation in the wearable absorbent hygiene article.

In one implementation, the impedance between the two plates in free space has a first value. The impedance between the second two plates has a second value. The first value and the second value are different.

As the properties of the two pairs of plates are different such that their impedance in free space is different, it is possible to tailor each pair of plates so as to be more sensitive to a particular type of soiling.

In one implementation, the method further comprises detecting a hygienic event by analyzing the impedance measured between the two plates.

With such a method, it is possible accurately to discriminate between a hygienic event and other local disturbances to the environment around the sensor strip.

In one implementation, the method further comprises detecting a hygienic event by analyzing the second impedance measured between the second two plates. The method may comprise detecting a hygienic event by analyzing the impedance measured between the two plates and by analyzing the impedance measured between the second two plates.

With such methods, it is possible accurately to discriminate between hygienic events localized in proximity to the second two plates, other local disturbances to the environment around the second two plates.

In one implementation, the hygienic event detected by analyzing the impedance and the hygienic event detected by analyzing the second impedance are the same hygienic event. The hygienic event may be urination or defecation.

With such a method, it is possible accurately to discriminate between hygienic events localized in proximity to the second pair of plates, other local disturbances to the environment around the second pair of plates.

In one implementation, the hygienic event detected by analyzing the impedance and the hygienic event detected by analyzing the second impedance are different hygienic events. One hygienic event may be urination and the other hygienic event is defecation.

With such a method, it is possible accurately to discriminate between hygienic events based on their spatial localization relative to the plates.

In one implementation, at least one or both of the plates of the two plates has a greater width than at least one or both of the plates of the second two plates. The hygienic event detected by analyzing the impedance may be defecation and the hygienic event detected by analyzing the second impedance may be urination.

With such a method, the electric fields emanating from the first pair of plates extend a greater distance than the electric fields emanating from the second pair of plates. As fecal matter does not tend to penetrate into the article during a soiling event, the fecal matter is disposed further away from the plates than urine.

Accordingly, with this method, it is possible to more accurately detect urination/fecal matter.

In certain implementations, the first pair of plates is disposed towards a back waist region of a wearable absorbent hygiene article. In certain implementations, the second pair of plates is disposed towards a front waist region of a wearable absorbent hygiene article.

In one implementation, the method further comprises identifying a hygiene article to which, among a range of hygiene articles, the hygiene monitoring device has been installed, by analyzing the impedance measured between the two plates.

With such a method, it is possible to confirm correct usage of the strip with the article to which it was intended to be used.

In certain implementations, the hygiene monitoring device is attached to a wearable hygiene article such that the longitudinal axis of the elongate flexible panel is substantially parallel to the longitudinal axis of the wearable absorbent hygiene article.

For all embodiments described herein, the back layer is liquid impermeable, and, optionally, the back layer is breathable or vapor permeable.

For all embodiments described herein, the hygiene monitoring device may be configured to be attachable to the outside surface of the back layer. Specifically, the hygiene monitoring device may be configured to be attachable to the surface of the back layer which is opposite to the surface of the back layer facing the absorbent core.

For all embodiments described herein, the elongate flexible panel may be an elongate flex PCB panel. Various components of the sensing panel, in particular, the plates, tracks and contacts, may be printed components.

For all embodiments described herein, the wearable absorbent hygiene article may be an open-type diaper, pant-type diaper, belted diaper, incontinence pad or sanitary napkin.

For all embodiments described herein, the hygienic event which is detected based on the measured impedance(s) may be the presence of liquid, such as urine, or the presence of feces.

For all embodiments described herein, the absorbent core may be adapted to absorb bodily liquids. The absorbent core may include a fluffed wood pulp component for wicking and structural integrity and a high absorbency material (or super absorbent) for containing liquids, or any other composition known in the art.

For all embodiments described herein, unless stated otherwise, all of the plates of the elongate flexible panel may have substantially the same length and width, and, optionally, may be substantially the same shape and size.

Throughout this disclosure, reference to a length/width of an element refers to the relevant dimension of the element when the element is laid out flat, and, if the element is extensible, whilst the element is in its fully extended configuration.

BRIEF DESCRIPTION OF THE DRAWINGS

The features and advantages of the invention will be appreciated upon reference to the following drawings. The accompanying drawings, which are incorporated in and constitute a part of this specification, illustrate one or more embodiments of the invention and, together with the general description given above and the detailed description given below, explain the one or more embodiments of the invention. For a better understanding of the present invention and to show how the same may be carried into effect, reference will now be made, by way of example only, to the accompanying drawings.

DETAILED DESCRIPTION

Figure 1:
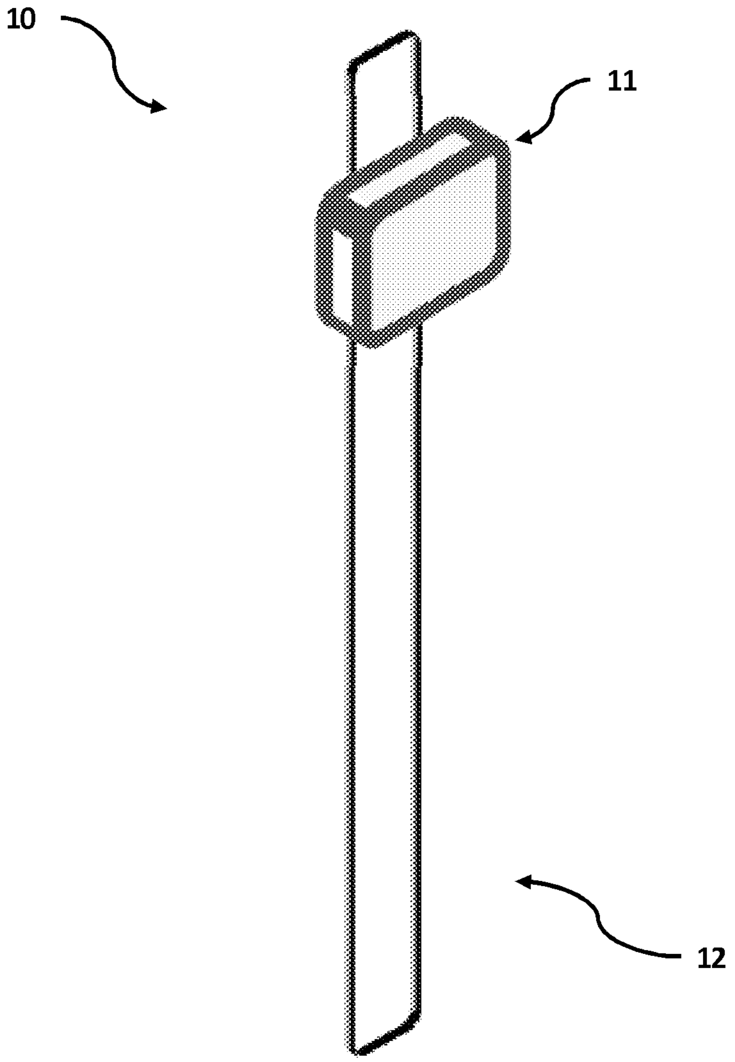
FIG. 1 is a perspective view of a hygiene monitoring device for monitoring the hygienic state of a user.

FIG. 1 shows a hygiene monitoring device 10 for monitoring a hygienic state of a user. The hygiene monitoring device 10 may be removably attached to a wearable article of a user so that it may monitor the hygienic state of the article. Specifically, the hygiene monitoring device 10 is removably attachable to the outside surface of the back layer 104 of the wearable absorbent article 100 (see FIGS. 4, 7A and 7B), although other configurations are also contemplated. To this end, the hygiene monitoring device 10 further comprises a hook and/or loop type fastener (not shown) configured to be removably attachable to the wearable absorbent hygiene article 100 which may optionally have a corresponding hook and/or loop type fastener (not shown). Other types of fasteners are contemplated herein.

The hygiene monitoring device 10 comprises a housing 11 and a sensing panel 12 in the form of a strip. The sensing panel 12 extends on both sides of the housing 11. However, in other embodiments, the sensing panel 12 may extend on only one side of the housing 11. The sensing panel 12 is in the form of an elongate flex PCB panel having various components printed thereon, as described below.

The hygiene monitoring device comprises a monitoring unit (not shown) removably provided to the sensing panel 12 which is configured to receive information (e.g., in the form of electrical signals) from the sensing panel 12 about the hygienic state of the article. In this embodiment, the monitoring unit is disposed in the housing 11. In some embodiments, the hygiene monitoring device 10 further comprises a transmitter (not shown) which is configured to transmit data to an external device, such as a centralised server (not shown). The hygiene monitoring device 10 is configured to transmit information relating to the monitored hygienic state of the article. In some embodiments, the hygiene monitoring device 10 may be configured to sound an alarm or provide another form of alert such as a visible or haptic indication when a particular hygienic state of the article is detected. In this embodiment, the transmitter is disposed in the housing 11.

Figure 2:
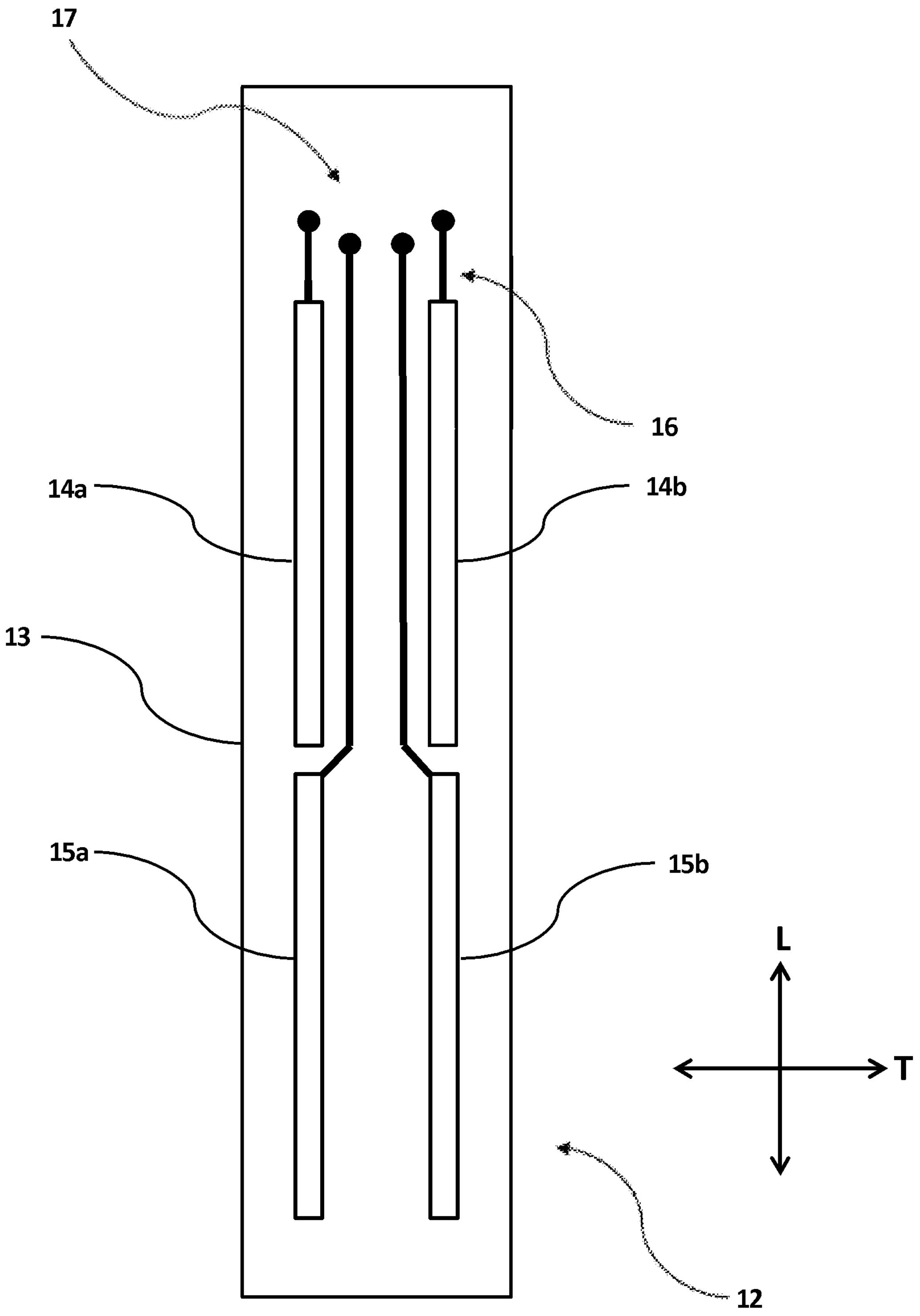
FIG. 2 is a plan view of the sensing panel of the hygiene monitoring device.

As shown in FIG. 2, the sensing panel 12 of the hygiene monitoring device 10 has an elongate flex PCB panel having a longitudinal axis L and a transverse axis T.

The elongate flex PCB panel comprises plates disposed on a flexible substrate 13 of the elongate flex PCB panel. The plates are each separated from one another other. As used herein 'plates' refer to electrically conductive plates.

Specifically, the elongate flex PCB panel has a first pair of plates 14*a*, 14*b* spaced apart from each other. The first pair of plates 14*a*, 14*b* are disposed on the flexible substrate 13 of the elongate flex PCB panel. The plates of the first pair of plates 14*a*, 14*b* are spaced apart or offset relative to each other along the transverse axis T of the elongate flex PCB panel. In other words, the plates of the first pair of plates 14*a*, 14*b* are spaced apart or offset relative to each other along the direction perpendicularly crossing the longitudinal axis L of the elongate flex PCB panel. In other embodiments, the plates of the first pair of plates 14*a*, 14*b* are spaced apart or offset relative to each other along any direction crossing the longitudinal axis L of the elongate flex PCB panel.

The pair of plates 14*a* and 14*b* are coplanar. Similarly, the pair of plates 15*a* and 15*b* are coplanar. Each of the plates 14*a*, 14*b*, 15*a* and 15*b* lies in the same plane as the flexible substrate.

The first pair of spaced apart plates 14*a*, 14*b* is configured to allow a measurement of an impedance therebetween by the monitoring unit.

As can be seen in FIG. 2, each plate of the first pair of spaced apart plates 14*a*, 14*b* is elongate along the longitudinal axis L of the elongate flex PCB panel. The longitudinal axes of the plates 14*a*, 14*b* are parallel to each other.

Each plate 14*a*, 14*b* is rectangular in shape.

The plates of the first pair of spaced apart plates 14*a*, 14*b* are substantially aligned along the longitudinal axis L of the elongate flex PCB panel.

A certain arrangement of the first pair of spaced apart plates 14*a*, 14*b* is given, however, as exemplified below, other shapes and arrangements of the plates are contemplated herein.

In addition to the first pair of plates 14*a*, 14*b*, the elongate flex PCB panel also has a second pair of plates 15*a*, 15*b* disposed on the flexible substrate 13. The second pair of plates 15*a*, 15*b* is similar to the above-described first pair of plates 14*a*, 14*b*, and, therefore, for brevity, no further details are given in this respect. All aspects described herein in relation to the first pair of plates 14*a*, 14*b* are equally applicable to the second pair of plates 15*a*, 15*b*.

As can be seen in FIG. 2, the first pair of spaced apart plates 14*a*, 14*b* and the second pair of spaced apart plates 15*a*, 15*b* are spaced apart along the longitudinal axis L of the elongate flex PCB panel. In other words, the first pair of spaced apart plates 14*a*, 14*b* is offset along the longitudinal axis L of the elongate flex PCB panel with respect to the second pair of spaced apart plates 15*a*, 15*b*.

In the embodiment shown in FIG. 2, the first pair of spaced apart plates 14*a*, 14*b* does not overlap along the longitudinal axis L of the elongate flex PCB panel with the second pair of spaced apart plates 15*a*, 15*b*. However, in alternative embodiments, the first pair of spaced apart plates 14*a*, 14*b* (at most) partially overlap along the longitudinal axis L of the elongate flex PCB panel with the second pair of spaced apart plates 15*a*, 15*b*.

Flexible substrate 13 is provided with tracks 16 and contacts 17 which are configured to allow each of the plates of the first pair of spaced apart plates 14*a*, 14*b* and the second pair of spaced apart plates 15*a*, 15*b* to be electrically coupled to the monitoring unit (not shown). For example, contacts of the monitoring unit (not shown) may contact the respective contacts 17 to electrically couple the respective plates with the monitoring unit (not shown).

The hygiene monitoring device 10 is configured such that the first pair of spaced apart plates 14*a*, 14*b* and the second pair of spaced apart plates 15*a*, 15*b* may be bought into the vicinity of the wearable article such that they may measure the hygienic state of the article, for example, by measurement of the impedance between the respective plates in each of the first pair of spaced apart plates 14*a*, 14*b* and the second pair of spaced apart plates 15*a*, 15*b*. Measurements of impedance between two plates may be carried out by any convenient method as known to the person skilled in the art.

Without wishing to be bound by any particular theory of operation, adjusting the geometry of the plates will adjust the extent to which the electric field lines between the plates extend into the surrounding environment. For example, the electric field lines between plates separated by an increased distance may penetrate more deeply into the local environment. Such an effect may be appreciated with reference to FIGS. 7A and 7B, which are explained in detail below. Therefore, they will be affected more strongly by a change in the environment at an increased distance from the plates.

The geometry of the plates may be determined based on the expected construction of the absorbent articles or range of absorbent articles with which the sensing panel 12 is to be used. For example, for use with absorbent articles having a particular thickness of absorbent material in an absorbent core, the spacing of the plates may be adjusted so as to ensure that the electric field lines between the plates penetrate into the core, but do not significantly penetrate beyond the core. Such a configuration permits the coupling between the plates to be sensitive to a change in the core, for example liquid absorption, but not to movements of the wearer's body. In other configurations, the spacing of the plates may be adjusted so as to allow the electric field lines between the plates only slightly to penetrate into the core.

In addition to the above, the hygiene monitoring device 10 is configured to measure the impedance between two plates in two different pairs of plates. In this particular embodiment, the hygiene monitoring device 10 is configured to individually measure the impedance between each and every possible combination of two plates. In particular, the hygiene monitoring device 10 is configured to individually measure the impedance between: plate 14*a* and plate 14*b*; plate 15*a* and plate 15*b*; plate 14*a* and plate 15*a*; plate 14*a* and plate 15*b*; plate 14*b* and plate 15*a*; and plate 14*b* and plate 15*b*.

In the situation where the impedance is measured between plate 14*a* and plate 15*b* or where the impedance is measured between plate 14*b* and plate 15*a*, the first plate (i.e., plate 14*a* or plate 14*b*, respectively) is on a first side of the elongate flex PCB panel along the transverse axis T, and the second plate (i.e., plate 15*b* or plate 15*a*, respectively) is on a second side of the elongate flex PCB panel along the transverse axis T, where the second side is opposite to the first side along the transverse axis T.

The hygiene monitoring device 10 may carry out a method comprising measuring the impedance between any of the two plates, and, optionally, measuring a second impedance between a different two plates.

For example, the hygiene monitoring device 10 may carry out a method comprising measuring an impedance between the plates of the first pair of spaced apart plates 14*a*, 14*b*. The measured impedance between the first pair of spaced apart plates 14*a*, 14*b* may be used to determine by the monitoring unit the hygienic state in a first area of the hygiene article.

In particular, the hygiene monitoring device may identify a hygienic event, such as a urinary or fecal insult, based on a change in the impedance between the plates. The change in the impedance may be detected based on a change in the magnitude of the impedance of the response of the plates at one or more frequencies. For example, a urinary insult may be associated with a change in the magnitude of the response of the plates at a given frequency, whereas a fecal insult may be associated with a different change in the magnitude of the response.

Further, the hygiene monitoring device may identify a hygienic event based on the response of the plates at a plurality of frequencies. For example, a urinary insult may be associated with a change in the magnitude of the impedance of the plates predominantly at one frequency, whereas a fecal insult may be associated with a change in the magnitude predominantly at a second, different frequency.

In one configuration, the hygiene monitoring device may associate a first characteristic frequency response of the plates with a first event, such as a urinary insult, and may associate a second characteristic frequency response of the plates with a second event, such as a fecal insult.

The method may further comprise measuring a second impedance between the plates of the second pair of spaced apart plates 15*a*, 15*b*. The measured second impedance may be used to determine by the monitoring unit the hygienic state in a second area of the hygiene article. Again, the hygiene monitoring device may identify a hygienic event based on a change in the impedance between the plates, and the change in the impedance may be detected based on a change in magnitude of the measured impedance.

The hygienic events detected by the analysis of the first impedance and the second impedance may be different, for example, the first event may be urination and the second event may be defecation. The monitoring device may discriminate between different events on the basis of the area associated with a pair of plates which provides the strongest response to a drive signal during the event. The monitoring device may also or alternatively discriminate between different events based on a consideration of the magnitude of the impedance measured between the plates at one or more frequencies. For example, the hygiene monitoring device may compare the response of one or both pairs of plates at one or more frequencies against a set of characteristic responses correlated with a corresponding set of distinct events, and select the event that most closely matches the response.

The hygiene monitoring device 10 may also carry out a method of confirming the installation of the sensing panel 12 to an intended article. For example, the response of one or both pairs of plates may differ depending on whether the sensing panel 12 is in free space, is in a storage configuration, or is arranged against an absorbent article. By confirming the response of one or both pairs of plates, the hygiene monitoring device may confirm that the strip has been correctly installed to the intended article, by a similar mechanism to the classification of different hygienic events as described above. Moreover, the hygiene monitoring device may confirm to which, among a range of hygiene articles, the strip has been installed, again based on a consideration of the magnitude of the response of one or both pairs of plates at one or more frequencies, again by a similar mechanism to the classification of different hygienic events as described above.

Figure 3:
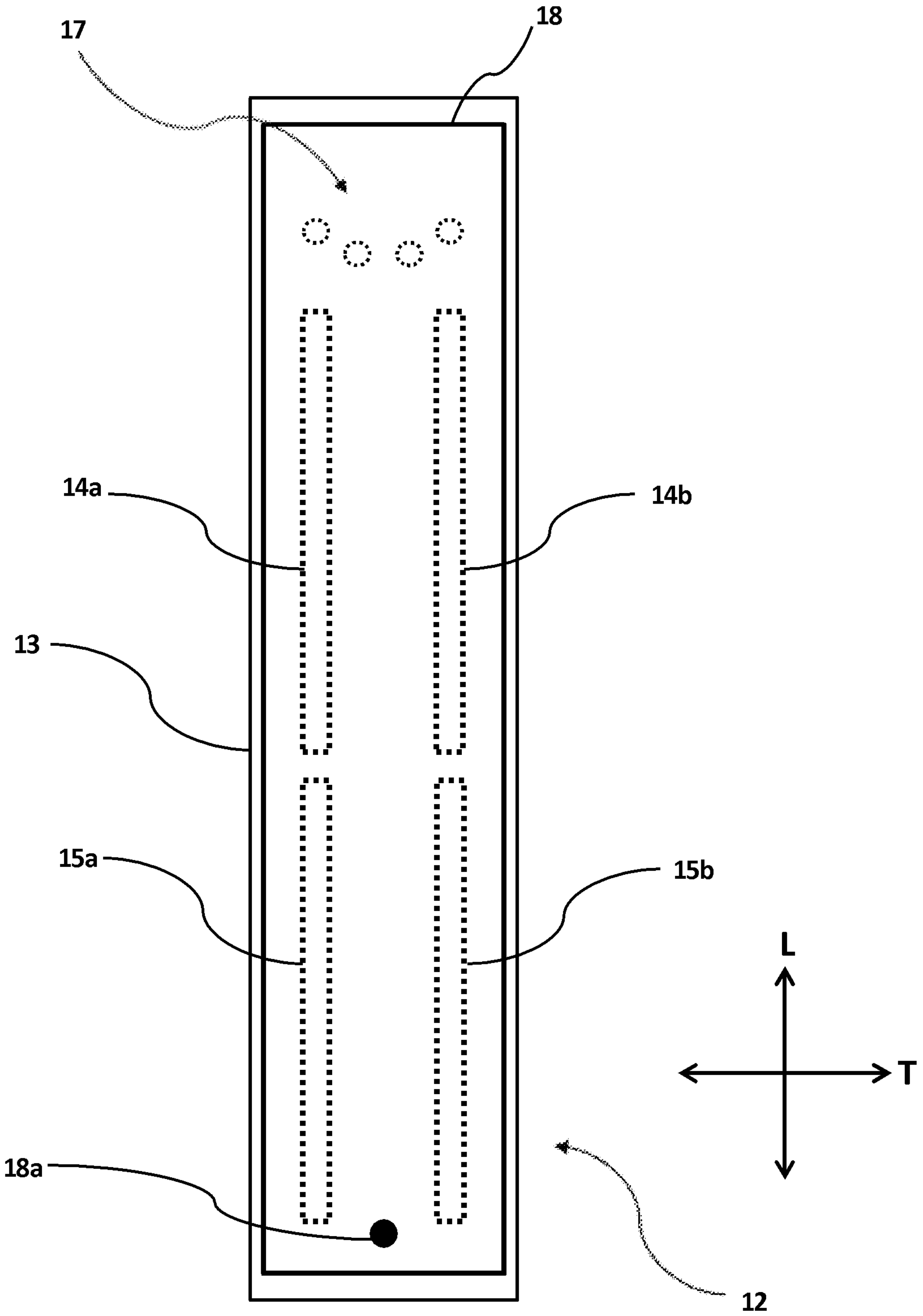
FIG. 3 is another plan view of the sensing panel of the hygiene monitoring device.

FIG. 2 shows various components/elements of the sensing panel 12 printed on a first side of the flexible substrate 13 of the elongate flex PCB panel. FIG. 3 shows the opposite side of the flexible substrate 13 and the various components/elements printed thereon.

As can be seen from FIG. 3, the elongate flex PCB panel further comprises a grounding plate 18 disposed on the opposite side of the flexible substrate 13 from the first pair of spaced apart plates 14*a*, 14*b* and the second pair of spaced apart plates 15*a*, 15*b*. A water-impermeable dielectric layer, such as a polymer coating, may cover the plates so as to protect the plates and to avoid moisture from inducing short-circuits between the plates.

In FIG. 3, the first pair of spaced apart plates 14*a*, 14*b*, the second pair of spaced apart plates 15*a*, 15*b* and the contacts 17 are shown with phantom lines. The tracks 16 are not shown for ease of illustration, however, they are arranged in the manner shown in FIG. 2.

The grounding plate 18 is disposed on the second side of the flexible substrate 13 and defines a contact 18*a* which may be connected to the ground (relative ground), for example, the ground in the monitoring unit.

The grounding plate 18 is arranged such that it entirely overlaps with the first pair of spaced apart plates 14*a*, 14*b*, the second pair of spaced apart plates 15*a*, 15*b*, the tracks 16 (not shown in FIG. 3), and the contacts 17. However, other arrangements of the grounding plate 18 are contemplated with only partial overlap.

The grounding plate 18 is configured to shield the electric fields emanating from the first pair of spaced apart plates 14*a*, 14*b*, and the second pair of spaced apart plates 15*a*, 15*b*. In other words, the grounding plate 18 is configured to attenuate the electric fields emanating from the first pair of spaced apart plates 14*a*, 14*b*, and the second pair of spaced apart plates 15*a*, 15*b*. By such a configuration, the electric fields emanating from the plates are directed primarily towards the first side of the flexible substrate 13.

Figure 4:
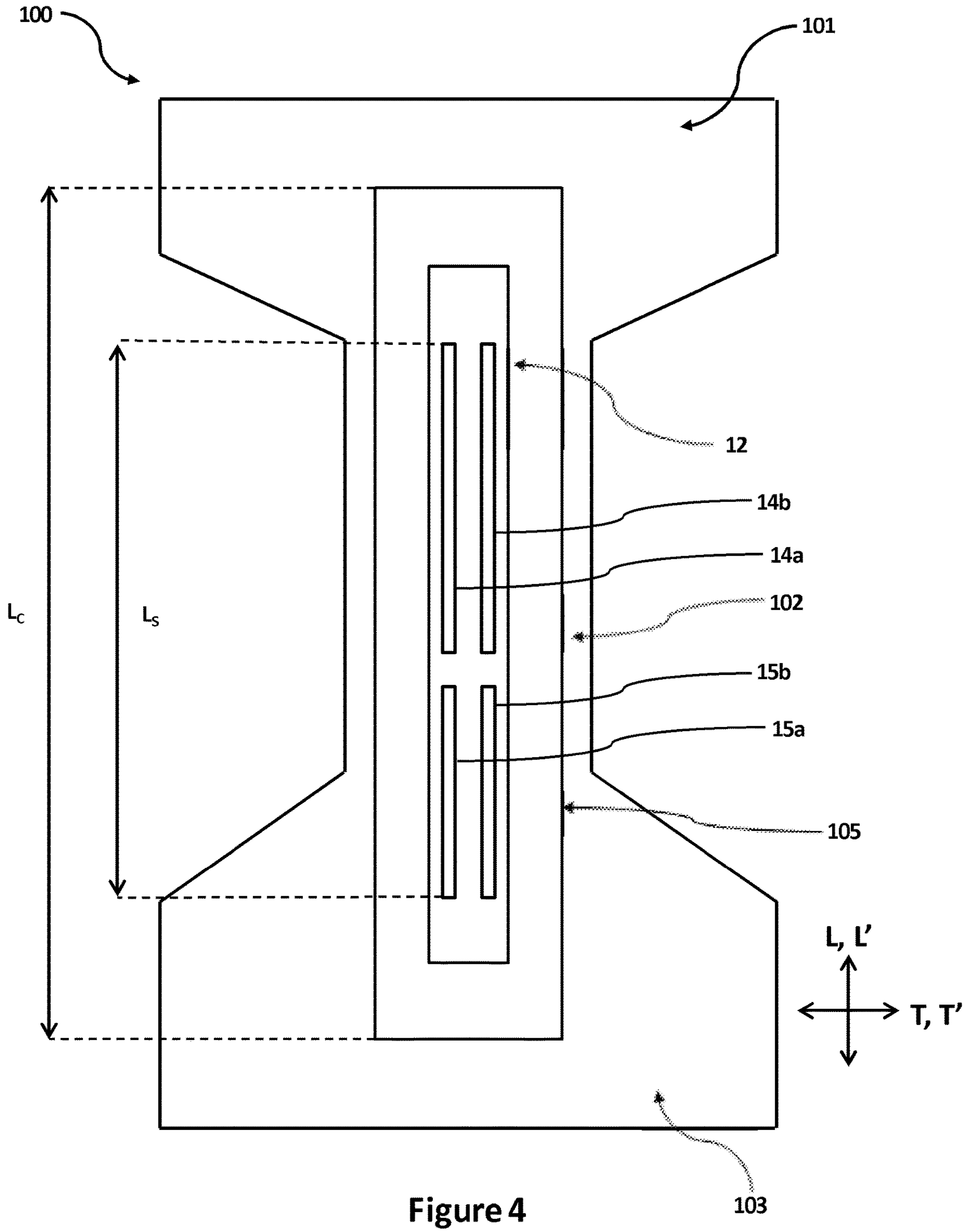
FIG. 4 is a plan view of a wearable absorbent hygiene article comprising the hygiene monitoring device.

FIG. 4 shows a wearable absorbent hygiene article 100 which has the hygiene monitoring device 10. In the embodiment shown in FIG. 4, the wearable absorbent hygiene article 100 is an open-type diaper, however other wearable absorbent hygiene articles are contemplated herein. For ease of illustration, the housing 11 of the hygiene monitoring device 10 is not shown in FIG. 4.

Figure 7A:
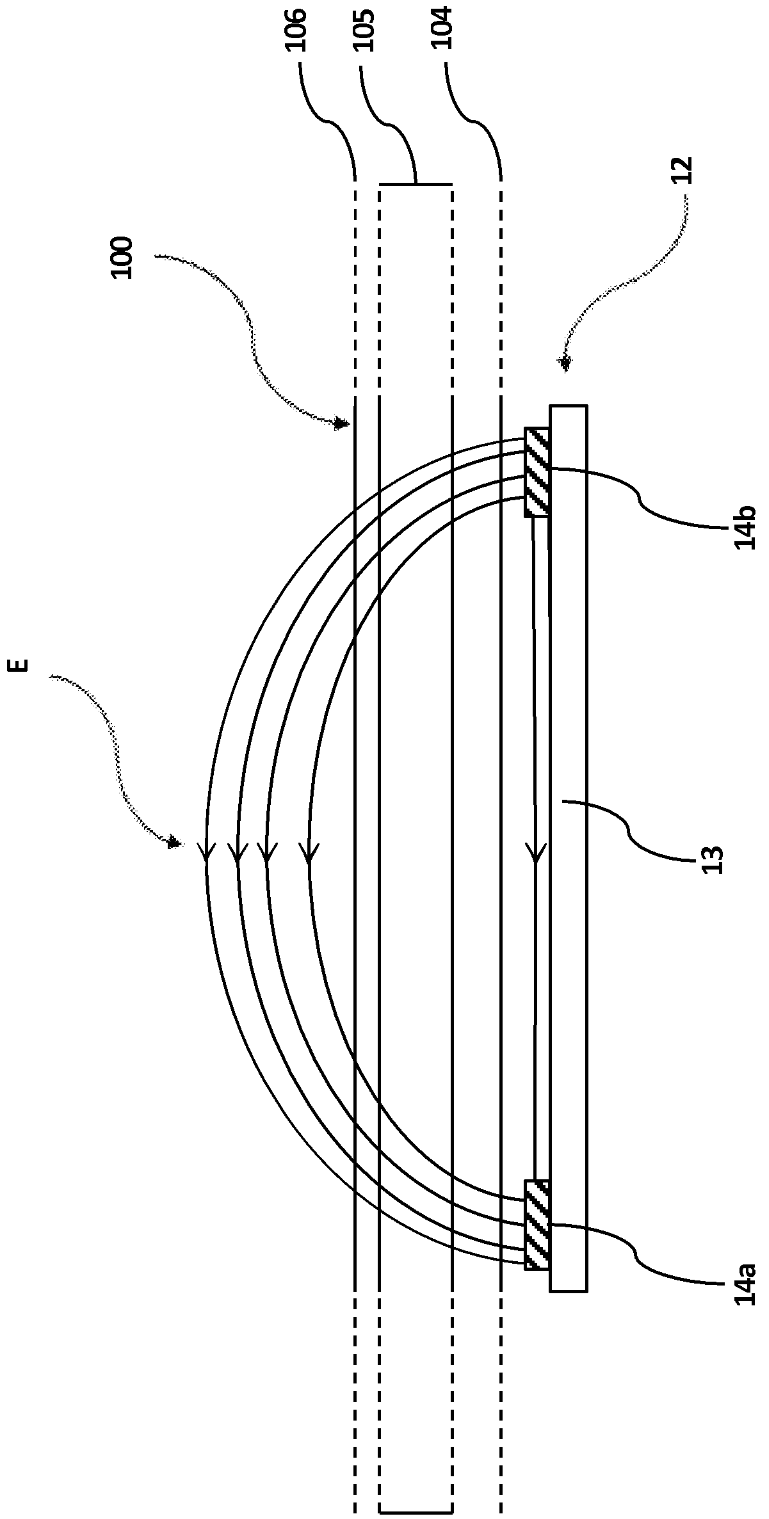
FIG. 7A is a cross-sectional view of the sensing panel of FIG. 6 in the proximity of an article.
Figure 7B:
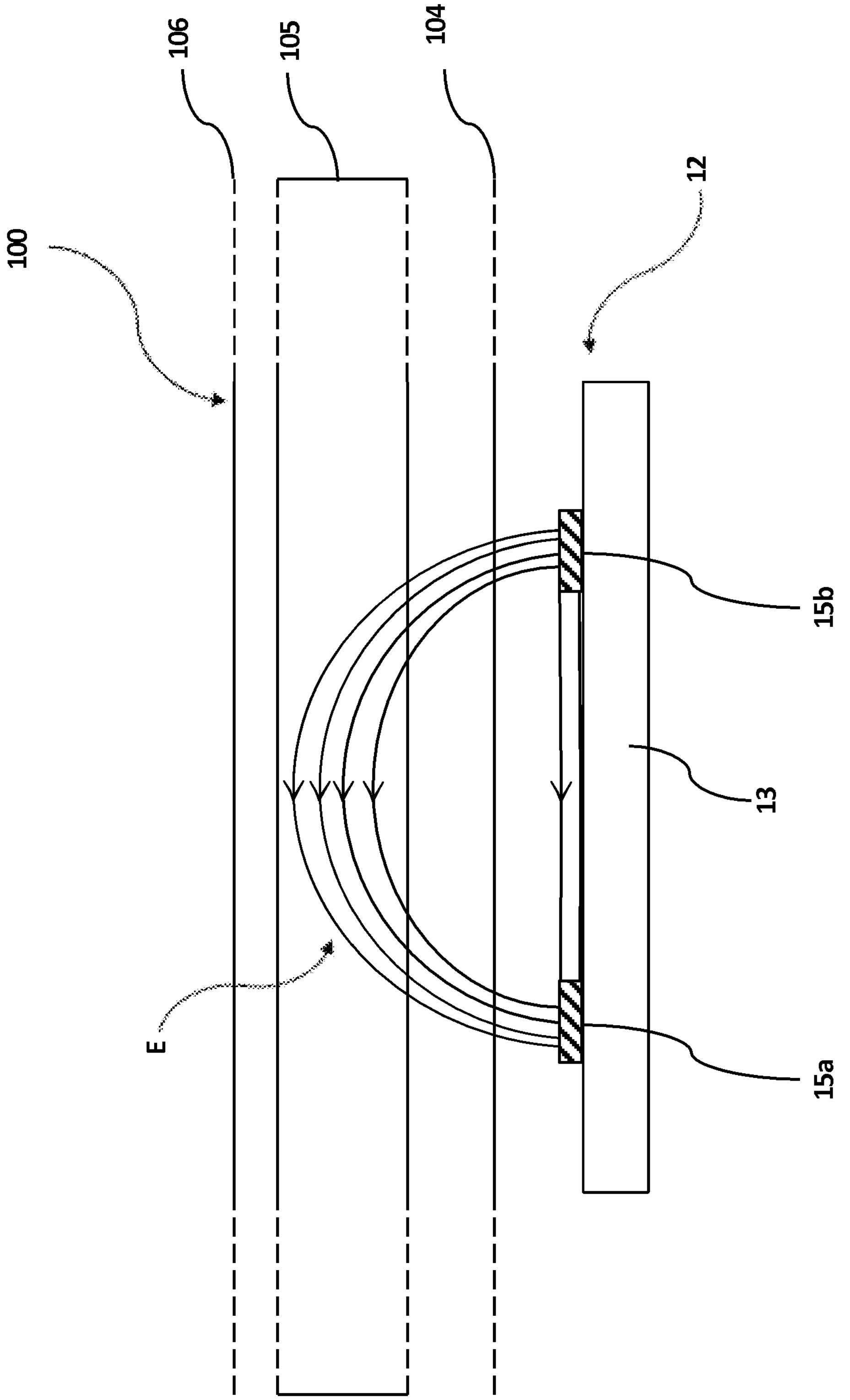
FIG. 7B is another cross-sectional view of the sensing panel of FIG. 6 in the proximity of an article.

The wearable absorbent hygiene article 100 defines a front waist region 101, a crotch region 102 and a back waist region 103. As shown in FIGS. 7A and 7B, the wearable absorbent hygiene article 100 comprises a liquid permeable top layer 106 adapted to face the wearer during use, a back layer 104 opposite to the top layer, and an absorbent member/core 105 located between the top layer 106 and the back layer 104.

The wearable absorbent hygiene article 100 defines a longitudinal axis L' and a perpendicular transverse axis T', as shown in FIG. 4 and as would be understood by the skilled person in the art.

The hygiene monitoring device 10 is disposed such that the longitudinal axis L of the sensing panel 12 (and the elongate flex PCB panel) is parallel to the longitudinal axis L' of the wearable absorbent hygiene article 100, as shown in FIG. 4.

In the embodiment shown in FIG. 4, the sensing panel 12, and, in particular, the elongate flex PCB panel extends in the waist region 101, the crotch region 102 and the back waist region 103. Furthermore, the plates have a longitudinal extent which extends in the waist region 101, the crotch region 102 and the back waist region 103.

The hygiene monitoring device 10, and, in particular, the sensing panel 12 may be configured to be disposed on the back layer opposite to the side of the absorbent member. In other words, the hygiene monitoring device 10, and, in particular, the sensing panel 12 may be configured to be disposed on the outer side of the back layer. For example, the hygiene monitoring device 10 may be removably attached to the back layer by any means, in particular, the sensing panel 12 may be removably attached to the back layer by a hook-and-loop fasteners such as VELCRO®. The sensing panel is configured to be arranged such that the plates are disposed entirely within the area defined by the absorbent core 105. However, it is also contemplated that the sensing panel is configured such that the plates extend partially outside the area defined by the absorbent core 105.

The absorbent core 105 has a core length $L_C$ along the longitudinal axis L' of the wearable absorbent hygiene article 100.

The extent of the plates along the longitudinal axis L of the elongate flex PCB panel defines a sensing length $L_S$. In other words, the opposing most longitudinally spaced points of the plates are separated by the sensing length $L_S$.

In the embodiment of FIG. 4, the sensing length $L_S$ is 75% of the core length $L_C$. However, it is contemplated that the sensing length $L_S$ may be 50% to 100% of the core length $L_C$.

Wearable absorbent hygiene articles suited for use with children may for example have an absorbent core with a core length $L_C$ of from 15 to 50 cm.

Sensors adapted for such hygiene articles may have sensing length $L_S$ of from 8, 15, 20 to 50, 40 or 30 cm.

Wearable absorbent hygiene articles suited for use with adults may for example have an absorbent core with a core length $L_C$ of from 40 to 100 cm.

Sensors adapted for such hygiene articles may have sensing length $L_S$ of from 20, 30, 40, to 100, 90, 80, 70 cm.

In other embodiments, the hygiene monitoring device 10, and, in particular, the sensing panel 12 may be disposed between the liquid permeable top layer and the back layer, and, in certain embodiments, between the absorbent member and the back layer. In such embodiments, the elongate flex PCB panel may comprise an insulating layer which entirely covers the plates.

Figure 5:
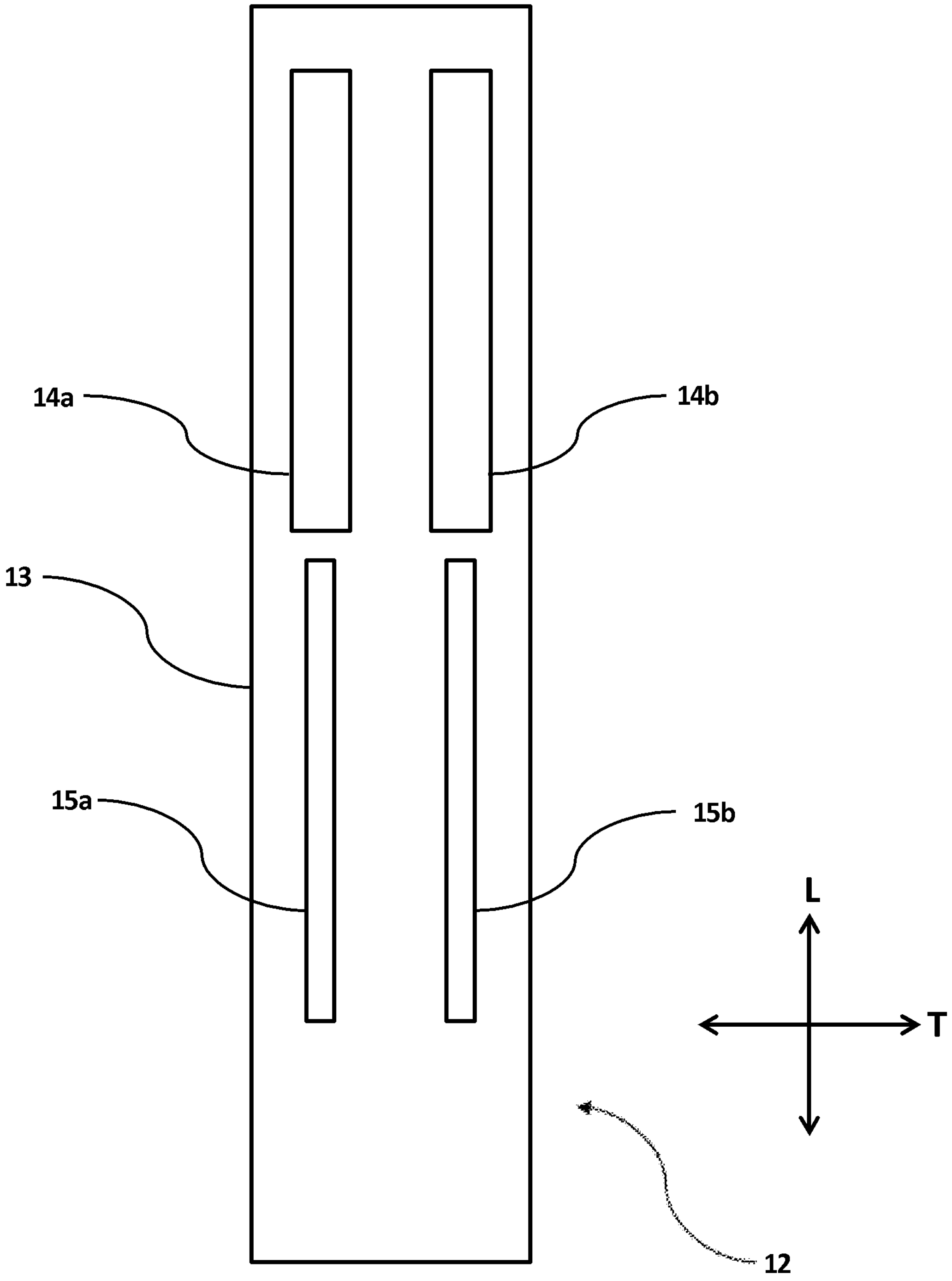
FIG. 5 is a plan view of an alternative embodiment of the sensing panel.

FIG. 5 shows an alternative embodiment of the sensing panel 12. The embodiment shown in FIG. 5 is similar to the embodiment shown in FIGS. 2 and 3 and includes similar elements. Accordingly, for brevity, only the differences are detailed below.

Specifically, as shown in FIG. 5, the plates of the first pair of spaced apart plates 14*a*, 14*b* have a greater width in the transverse direction T of the elongate flex PCB panel than the plates of the second pair of spaced apart plates 15*a*, 15*b*.

The first pair of spaced apart plates 14*a*, 14*b* thereby is more responsive to material which does not penetrate deeply into an absorbent article against which the sensing panel is arranged. Accordingly, the first pair of spaced apart plates 14*a*, 14*b* is configured to detect fecal matter, which tends to be absorbed with greater difficulty into an absorbent core, and which may lie on the surface thereof after an insult. The second pair of spaced apart plates 15*a*, 15*b* thereby is more responsive to material which penetrates deeply into an absorbent article against which the sensing panel is arranged. Accordingly, the second pair of spaced apart plates 15*a*, 15*b* is configured to detect urine, which tends to be absorbed with greater ease into an absorbent core, and which may wholly be absorbed therein.

The first pair of spaced apart plates 14*a*, 14*b* is configured to be disposed towards the back waist region 103 of the wearable absorbent hygiene article 100.

The second pair of spaced apart plates 15*a*, 15*b* is configured to be disposed towards the front waist region 101 of the wearable absorbent hygiene article 100.

Figure 6:
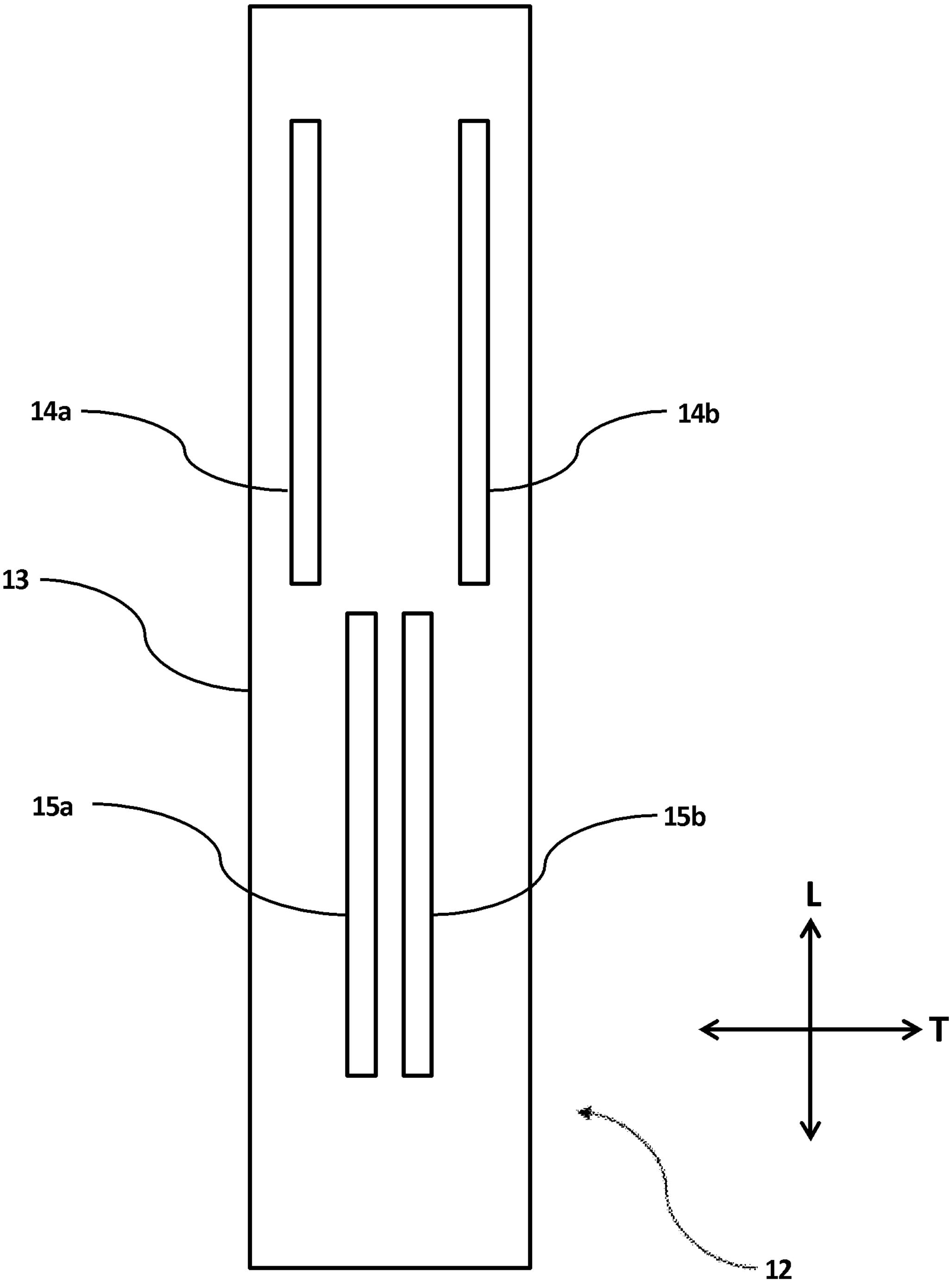
FIG. 6 is a plan view of another alternative embodiment of the sensing panel.

FIG. 6 shows another alternative embodiment of the sensing panel 12. The embodiment shown in FIG. 6 is similar to the embodiment shown in FIGS. 2 and 3 and includes similar elements. Accordingly, for brevity, only the differences are detailed below.

Specifically, as shown in FIG. 6, the plates of the first pair of spaced apart plates 14*a*, 14*b* are spaced-apart in the transverse direction T a greater distance than the plates of the second pair of spaced apart plates 15*a*, 15*b*.

The first pair of spaced apart plates 14*a*, 14*b* is configured to be disposed towards the back waist region 103 of the wearable absorbent hygiene article 100.

The second pair of spaced apart plates 15*a*, 15*b* is configured to be disposed towards the front waist region 101 of the wearable absorbent hygiene article 100.

FIGS. 7A and 7B each show a cross section of a wearable absorbent hygiene article 100 with the sensing panel 12 of FIG. 6 disposed on the back layer 104 of the wearable absorbent hygiene article 100. FIG. 7A shows a cross section including the first pair of spaced apart plates 14*a*, 14*b* and FIG. 7B shows a cross section including the second pair of spaced apart plates 15*a*, 15*b*.

Not wishing to be bound by theory, FIGS. 7A and 7B additionally show the typical electric fields E between the pairs of plates, where in each case, the plates 14*a* and 15*a* are negatively charged and the plates 14*b* and 15*b* are positively charged.

As shown in FIGS. 7A and 7B, the electric fields E between the first pair of spaced apart plates 14*a*, 14*b* tend to extend further away from the substrate 13 than the electric fields E between the second pair of spaced apart plates 15*a*, 15*b*.

The strength of the electric field E between the first pair of spaced apart plates 14*a*, 14*b* above the top layer 106 (i.e., on the wearer-facing side of the top layer 106) is greater than the strength of the electric field E between the second pair of spaced apart plates 15*a*, 15*b*.

The first pair of spaced apart plates 14*a*, 14*b* thereby is more responsive to material which does not penetrate deeply into an absorbent article against which the sensing panel is arranged. Accordingly, the first pair of spaced apart plates 14*a*, 14*b* is configured to detect fecal matter, which tends to be absorbed with greater difficulty into the absorbent core 105, and which may lie on the surface thereof after an insult. The second pair of spaced apart plates 15*a*, 15*b* thereby is more responsive to material which penetrates deeply into an absorbent article against which the sensing panel is arranged. Accordingly, the second pair of spaced apart plates 15*a*, 15*b* is configured to detect urine, which tends to be absorbed with greater ease into the absorbent core 105, and which may wholly be absorbed therein.

Figure 8:
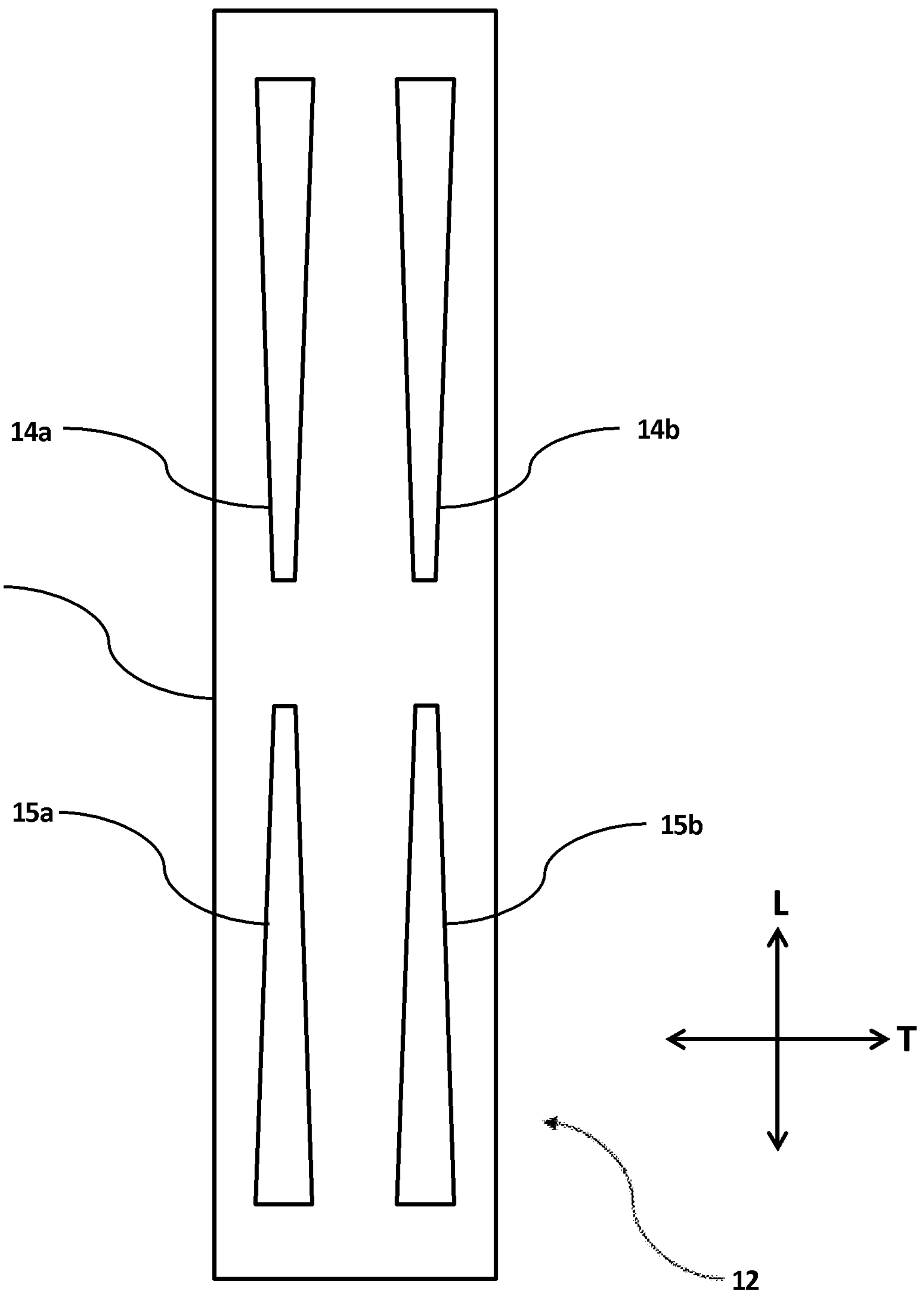
FIG. 8 is a plan view of a further alternative embodiment of the sensing panel.

FIG. 8 shows another alternative embodiment of the sensing panel 12. The embodiment shown in FIG. 6 is similar to the embodiment shown in FIGS. 2 and 3 and includes similar elements. Accordingly, for brevity, only the differences are detailed below.

Specifically, as shown in FIG. 8, each of the plates of the first pair of spaced apart plates 14*a*, 14*b* and each of the plates of the second pair of spaced apart plates 15*a*, 15*b* have a tapered shape. In other words, each of the plates has a width which decreases moving along the longitudinal axis of the plate. By the decreasing width, an increased gap is provided between the respective plates moving along the longitudinal axis. With an increased gap, as described above, the plate becomes more sensitive to the environment at a greater distance. The plates of FIG. 6 therefore exhibit an increased distance sensitivity at one longitudinal end than the other.

Figure 10:
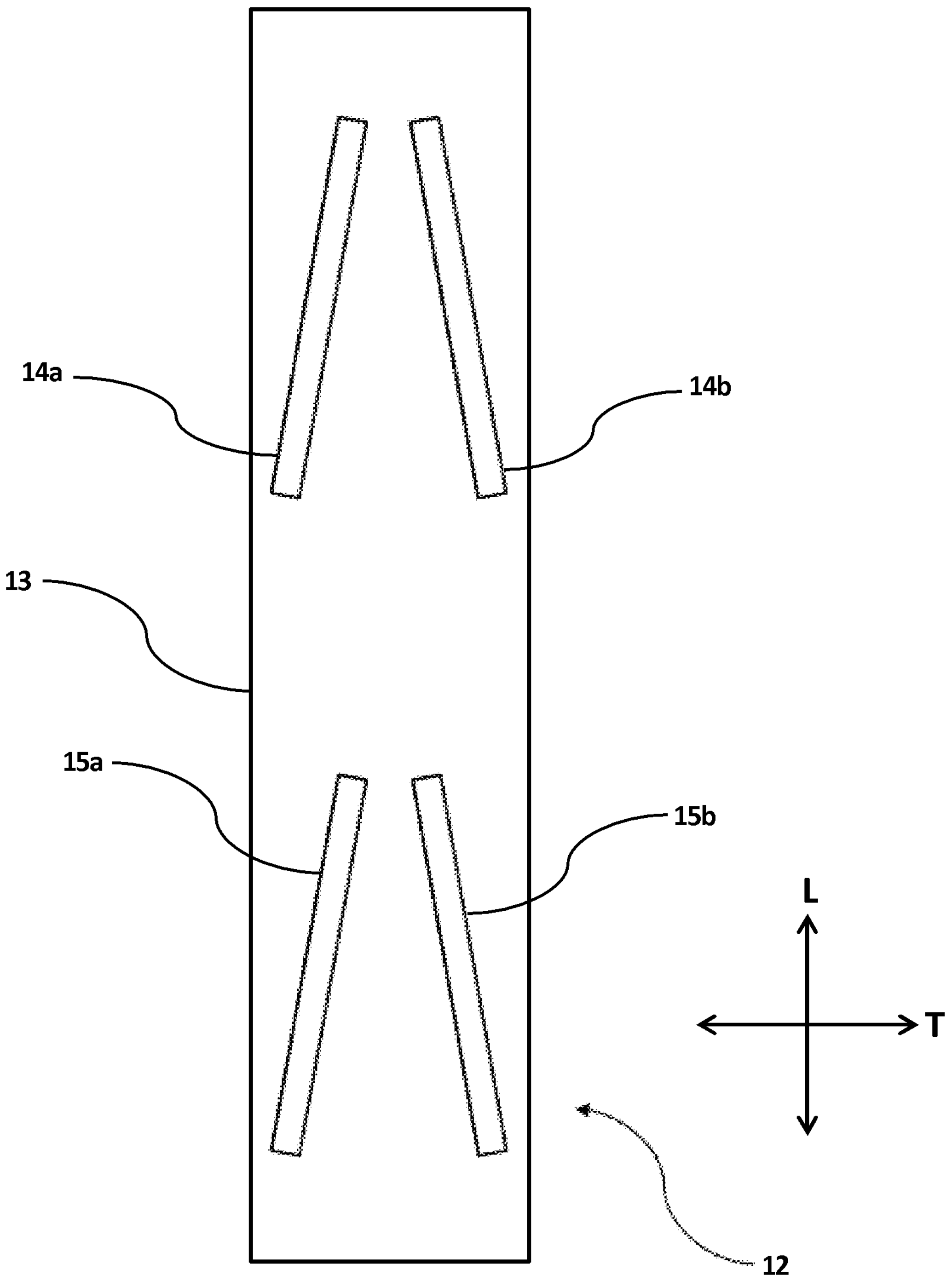
FIG. 10 is a plan view of another alternative embodiment of the sensing panel.

In the embodiment shown in FIG. 8, the width decreases along the entire length of the plates. However, in alternative embodiments, the width decreases along only a portion of the length of the plates. In other words, the plates comprise a tapered portion. In other alternative embodiments, as shown in FIG. 10, the plates may not themselves be tapered, but may be arranged to converge along the longitudinal axis of the sense strip, with similar effects.

As shown in FIG. 8, the narrower portions of the plates are disposed towards the center of the elongate flex PCB panel. Such a configuration may have improved discrimination between hygienic events and movements of the user's body at such a region. However, in alternative embodiments, the wider portions of the first pair of spaced apart plates 14*a*, 14*b* and/or the narrower portions of the second pair of spaced apart plates 15*a*, 15*b* may be disposed towards the center of the elongate flex PCB panel. Such a configuration may improve response time to a hygienic event taking place in the vicinity of the center of the panel.

In an alternative configuration to that shown in FIG. 8, only a single pair of plates 14*a*, 14*b* may be provided, exhibiting a large-spacing portion at a first end of the strip and a small-spacing portion at a second end of the strip. Yet further alternatively, such a single pair of plates may have a large-spacing portion (or a small-spacing portion) at the ends, and a corresponding small-spacing portion (or a large-spacing portion) between the ends. As above, the large-spacing portion and the small-spacing portion may be formed by changing the width of the plates, inclining the plates, or both.

Figure 9:
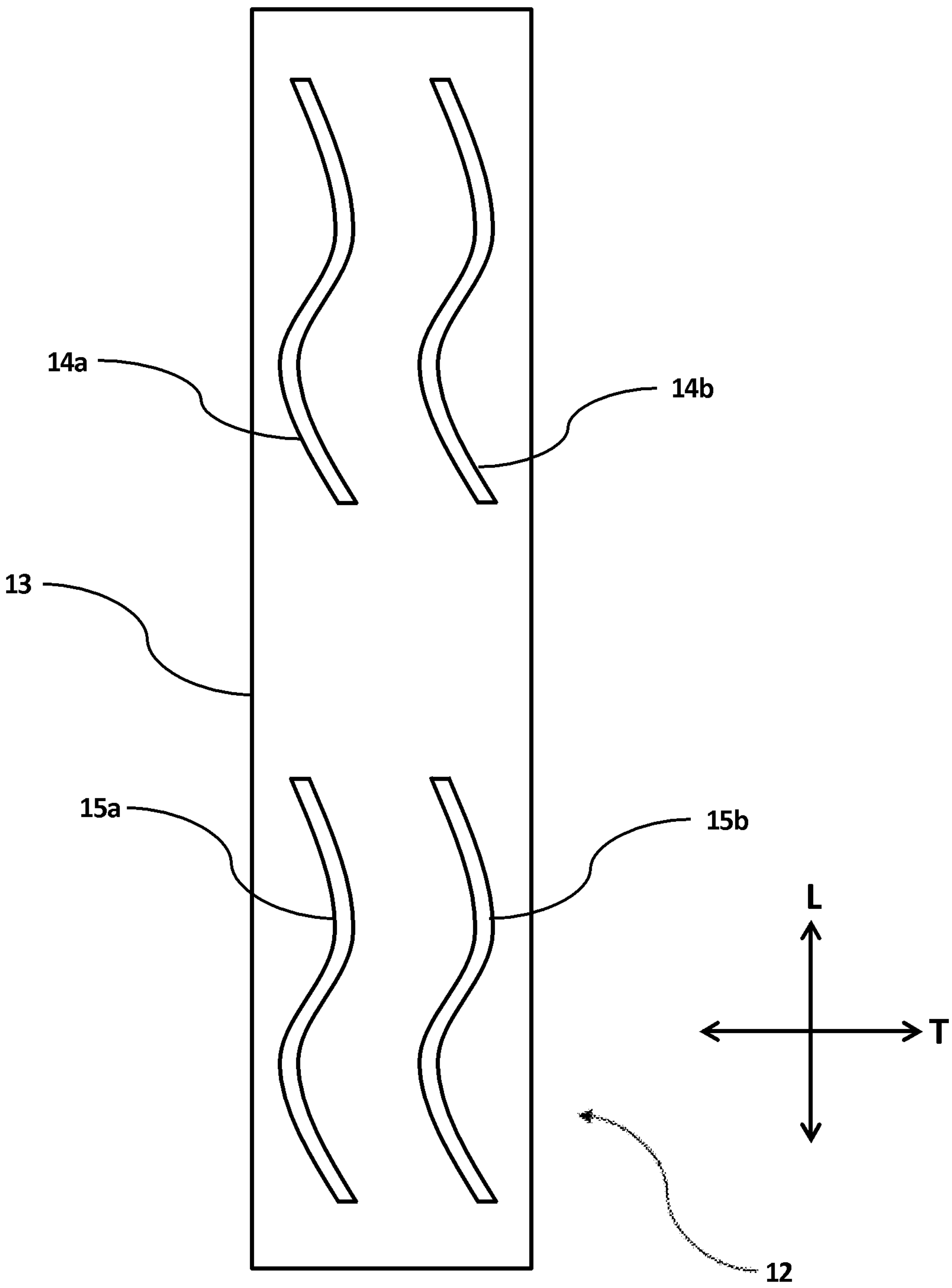
FIG. 9 is a plan view of yet another alternative embodiment of the sensing panel.

FIG. 9 shows another alternative embodiment of the sensing panel 12. The embodiment shown in FIG. 9 is similar to the embodiment shown in FIGS. 2 and 3 and includes similar elements. Accordingly, for brevity, only the differences are detailed below.

Specifically, as shown in FIG. 9, each of the plates of the first pair of spaced apart plates 14*a*, 14*b* and each of the plates of the second pair of spaced apart plates 15*a*, 15*b* have a wavy shape, which is a specific form of curved shape.

The above disclosure may be extended to three, four, five or more pairs of plates longitudinally arranged.

Figure 11:
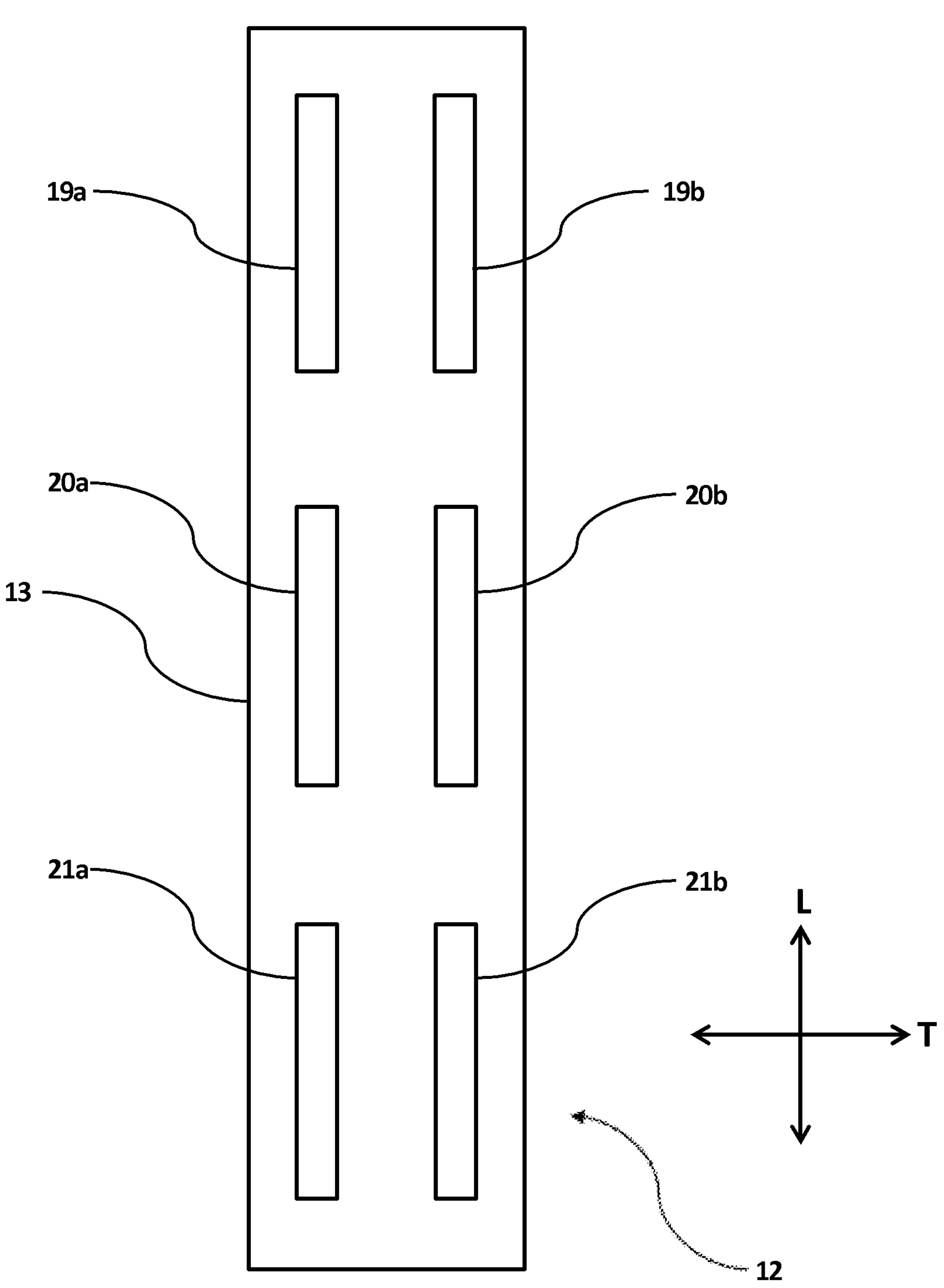
FIG. 11 is a plan view of a further alternative embodiment of the sensing panel.

For example, FIG. 11 shows another alternative embodiment of the sensing panel 12. The embodiment shown in FIG. 11 is similar to the embodiment shown in FIGS. 2 and 3 and includes similar elements. Accordingly, for brevity, only the differences are detailed below.

Specifically, as shown in FIG. 11, the sensing panel 12 comprises: a first pair of plates 19*a*, 19*b*, and second pair of plates 20*a*, 20*b*, and the third pair of plates 21*a*, 21*b*. The first pair of plates 19*a*, 19*b*, the second pair of plates 20*a*, 20*b*, and the third pair of plates 21*a*, 21*b* are each offset from each other along longitudinal axis L of the elongate flex PCB panel. The second pair of plates 20*a*, 2*b* is disposed in the longitudinal direction L between the first pair of plates 19*a*, 19*b* and the third pair of plates 21*a*, 21*b*.

These pairs of plates are arranged and configured in a similar manner to the pairs of plates 14*a*, 14*b* and 15*a*, 15*b* as described in any of the above embodiments.

The hygiene monitoring 10 may be configured to measure the impedance at least between a plate in the first pair of plates 19*a*, 19*b* and a plate in the third pair of plates 21*a*, 21*b*.

The hygiene monitoring 10 may also be configured to measure the impedance also between a plate in the first pair of plates 19*a*, 19*b* and a plate in the second pair of plates 20*a*, 20*b*. Additionally or alternatively, the hygiene monitoring 10 may also be configured to measure the impedance also between two plates in the same pair of plates (i.e., between plates 19*a* and 19*b*; plates 20*a* and 20*b*; or plates 21*a* and 21*b*).

The hygiene monitoring device 10 may be configured to individually measure the impedance between each and every possible combination of two plates.

Figure 12:
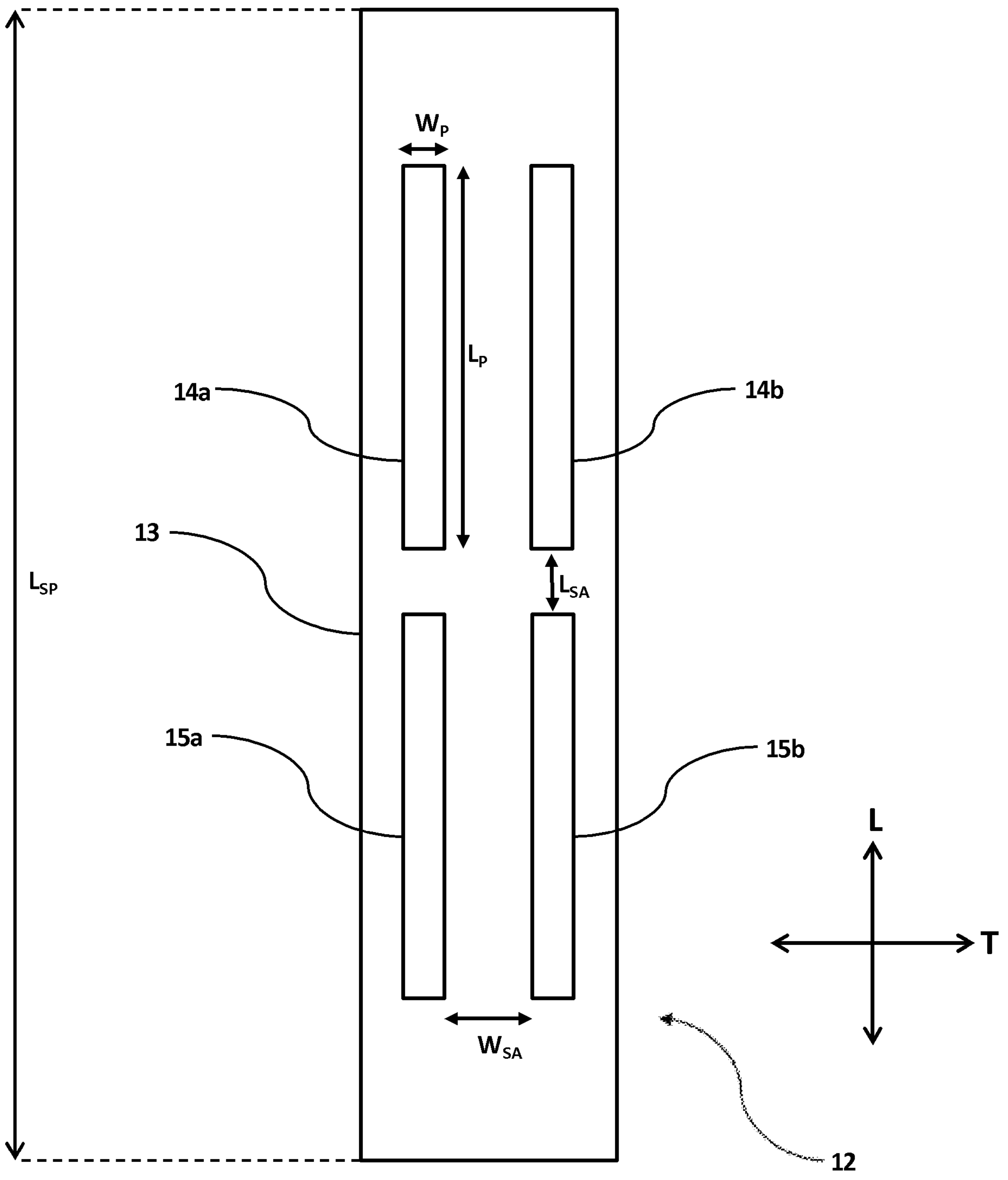
FIG. 12 shows dimensions of an embodiment of the sensing panel.

FIG. 12 shows the embodiment of the sensing panel 12 shown in FIGS. 2 and 3 with certain elements omitted for ease of illustration.

As can be seen in FIG. 12, each plate has a width $W_P$ in the transverse direction T of the elongate flex PCB panel and a length $L_P$ in the longitudinal direction L of the elongate flex PCB panel.

As can be seen in FIG. 12, the plates in each pair of plates are spaced apart along the transverse direction T of the elongate flex PCB panel by a distance $W_{SA}$. The plates of the first pair of plates 14*a*, 14*b* are offset along the longitudinal axis with respect to the plates of the second pair of plates 15*a*, 15*b* by a distance $L_{SA}$.

In the embodiment of FIG. 12, the width $W_P$ is 6 mm for all plates. It is contemplated herein that the width $W_P$ may be between 4 mm and 7 mm.

In the embodiment of FIG. 12, the length $L_P$ is 200 mm. It is contemplated herein that the length $L_P$ may be between 45 mm to 1000 mm, preferably between 180 mm and 220 mm.

In the embodiment of FIG. 12, the distance $W_{SA}$ is 6 mm. It is contemplated herein that the distance $W_{SA}$ may be between 4 mm and 7 mm.

In the embodiment of FIG. 12, the distance $L_{SA}$ is 6 mm. It is contemplated herein that the distance $L_{SA}$ may be between 4 mm and 7 mm.

Preferably, the distance $W_{SA}$ and the distance $L_{SA}$ are the same.

The elongate flex PCB panel has a length $L_{SP}$ in the longitudinal direction L. The length $L_P$ may be between 20% to 40%, preferably 30% of the length $L_{SP}$.

Although the above explanation is considered to fully clarify how the present disclosure may straightforwardly be put into effect by those skilled in the art, it is to be regarded as purely exemplary.

For example, even though the above embodiments describe two or more pairs of spaced apart electrodes, it is contemplated that the hygiene monitoring device comprises a different number of pairs of spaced apart electrodes. For example, the hygiene monitoring device may comprise only a single pair of spaced apart electrodes.

In the configurations where the hygiene monitoring device comprises a single pair of plates, the plates may be spaced apart along the transverse direction T and/or the longitudinal direction L of the flex PCB panel.

Furthermore, even though in the above embodiments the plates of the pairs of spaced apart electrodes are the same, it is possible that the plates are different. For example, the plate 14*a* and the plate 14*b* may have different shapes. Additionally or alternatively, the plate 15*a* and the plate 15*b* may have different shapes. For example, the plates may be substantially linear, may have a zig-zag form, a sinusoidal form, or an irregular form.

Additionally, even though in the above embodiment, the hygiene monitoring device 10 is configured to individually measure the impedance between each and every possible combination of two plates, it is contemplated that the hygiene monitoring device 10 is configured to measure the impedance between a single two plates.

Furthermore, even though in the above embodiment, the hygiene monitoring device 10 comprises an elongate flex PCB panel, it is contemplated that other panels may be used. For example, the hygiene monitoring device may comprise an elongate flexible panel of any kind. The further components, in particular, the plates, tracks and contacts may be formed by any means known in the art.

All of the above are fully in the scope of the disclosure, and are considered to form the basis for alternative embodiments in which one or more combinations of the above described features are applied, without limitation to the specific combinations disclosed above.

In light of this, there will be many alternatives which implement the teaching of the present disclosure. It is expected that one skilled in the art will be able to modify and adapt the above disclosure to suit their own circumstances within the scope of the present disclosure, while retaining some or all technical effects of the same, either disclosed or derivable from the above, in light his common general knowledge in this art. All such equivalent modifications or adaptations fall within the scope of the present invention as defined by the appended claims.

The embodiments described above are descriptions of preferred embodiments of the present invention, and are not intended to limit the scope of the present invention. Various variations and modifications can be made by those of ordinary skill in the art, without departing from the design and scope of the present invention. The variations and modifications should all fall within the claimed scope defined by the claims of the present invention.

What is claimed is:

1. A hygiene monitoring device configured to be attached to a wearable absorbent article and comprising a sensing panel, the sensing panel comprising:

an elongate flexible substrate defining a longitudinal axis, a first pair of plates spaced apart from each other in a transverse direction crossing the longitudinal axis of the elongate flexible substrate, and a second pair of plates spaced apart from each other in the transverse direction, wherein the first pair of plates and the second pair of plates are disposed on the elongate flexible substrate, wherein each plate of the first pair of plates and each plate of the second pair of plates is elongate along the longitudinal axis of the elongate flexible substrate, wherein an entirety of each plate of the first pair of plates and the second pair of plates overlaps the elongate flexible substrate, wherein each of the first pair of plates and the second pair of plates are disposed parallel to the longitudinal axis of the elongate flexible substrate, wherein the first pair of plates is offset along the longitudinal axis of the elongate flexible substrate with respect to the second pair of plates, and wherein the hygiene monitoring device is configured to measure an impedance between two of the plates.

2. The hygiene monitoring device of claim 1, wherein the plates are disposed on one side of the elongate flexible substrate, wherein a grounding plate is disposed on the other side of the elongate flexible substrate, wherein the grounding plate partially or fully overlaps the plates in a plane of the elongate flexible substrate.

3. The hygiene monitoring device of claim 1, wherein a longest side of each of the plates of the first pair of plates are parallel, and wherein a longest side of each of the plates of the second pair of plates are parallel.

4. The hygiene monitoring device of claim 1, wherein at least one of the plates has a generally rectangular, tapered or curved shape.

5. The hygiene monitoring device of claim 1, wherein an impedance between the plates of the first pair of plates in free space has a first value, wherein an impedance between the plates of the second pair of plates in free space has a second value, and wherein the first value and the second value are different.

6. The hygiene monitoring device of claim 1, wherein at least one of the plates of the first pair of plates has a different shape from at least one of the plates of the second pair of plates.

7. The hygiene monitoring device of claim 1, wherein the plates of the first pair of plates are spaced apart a first distance, wherein the plates of the second pair of plates are spaced apart a second distance, and wherein the first distance and the second distance are different.

8. The hygiene monitoring device of claim 1, comprising a monitoring unit electrically connected to each of the plates, wherein the monitoring unit is configured to measure the impedance between the two plates.

9. The hygiene monitoring device of claim 1, wherein the two plates are plates in the same pair of plates.

10. The hygiene monitoring device of claim 1, wherein the two plates are plates in different pairs of plates.

11. The hygiene monitoring device of claim 10, wherein the first plate of the two plates is on a first side of the elongate flexible substrate along a thickness direction, and wherein the second plate of the two plates is on a second, opposite side of the elongate flexible substrate along the thickness direction.

12. The hygiene monitoring device of claim 1, wherein the elongate flexible substrate further comprises a third pair of plates spaced apart from each other in the transverse direction, the third pair of plates being disposed on the elongate flexible substrate, wherein the third pair of plates is offset along the longitudinal axis of the elongate flexible substrate with respect to each of the first and second pair of plates, and wherein the second pair of plates is disposed along the longitudinal axis of the elongate flexible substrate between the first pair of plates and the second pair of plates.

13. The hygiene monitoring device of claim 1, wherein the two plates are plates in the same pair of plates, and wherein the hygiene monitoring device is further configured to measure a second impedance between a second two of the plates, the second two plates being plates in different pairs of plates.

14. The hygiene monitoring device of claim 1, wherein an insulating layer entirely covers the plates.

15. The hygiene monitoring device of claim 1, wherein the hygiene monitoring device is configured to be removably attachable to the wearable absorbent hygiene article, wherein the hygiene monitoring device further comprises a hook and/or loop type fastener configured to be removably attachable to the wearable absorbent hygiene article, wherein the hook and/or loop type fastener is disposed on the elongate flexible substrate.

16. The hygiene monitoring device of claim 1, wherein the hygiene monitoring device comprises a pressure sensitive adhesive configured to allow the hygiene monitoring device to be attached to the wearable absorbent hygiene article.

17. A system, comprising:

a wearable absorbent hygiene article defining a front waist region, a back waist region, a crotch region and a longitudinal axis, the wearable absorbent hygiene article comprising:

a liquid permeable top layer adapted to face a wearer during use;

a back layer opposite to the top layer; and an absorbent core in at least the crotch region and located between the top layer and the back layer; and a hygiene monitoring device attached to the wearable absorbent hygiene article and comprising a sensing panel, the sensing panel comprising an elongate flexible substrate, a first pair of plates spaced apart from each other in a transverse direction crossing the longitudinal axis of the wearable absorbent hygiene article, and a second pair of plates spaced apart from each other in the transverse direction, wherein the elongate flexible substrate is disposed on a different layer from the top layer, the back layer, and the absorbent core, wherein an entirety of the elongate flexible substrate overlaps the absorbent core along a thickness direction of the wearable absorbent hygiene article, wherein the first pair of plates and the second pair of plates are disposed on the elongate flexible substrate, wherein each plate of the first pair of plates and each plate of the second pair of plates is elongate along the longitudinal axis of the wearable absorbent hygiene article, wherein an entirety of each plate of the first pair of plates and each plate of the second pair of plates overlaps the elongate flexible substrate along the thickness direction of the wearable absorbent hygiene article, wherein the first pair of plates is offset along the longitudinal axis of the wearable absorbent hygiene article with respect to the second pair of plates, and wherein the hygiene monitoring device is configured to measure an impedance between two of the plates.

18. The system of claim 17, wherein the hygiene monitoring device is configured to be attachable to the back layer of the wearable absorbent hygiene article, and wherein the hygiene monitoring device and the back layer each comprise corresponding hook and loop type fasteners.

19. A method carried out by the hygiene monitoring device of claim 1, the method comprising measuring the impedance between the two plates.

* * * * *